(12) United States Patent
Hu et al.

(10) Patent No.: US 11,027,050 B2
(45) Date of Patent: Jun. 8, 2021

(54) REDUCED PRESSURE TISSUE THERAPY DEVICE

(71) Applicant: KCI Licensing, Inc., San Antonio, TX (US)

(72) Inventors: Dean Hu, San Leandro, CA (US); Kenneth Wu, San Francisco, CA (US)

(73) Assignee: KCI Licensing, Inc., San Antonio, TX (US)

( * ) Notice: Subject to any disclaimer, the term of this patent is extended or adjusted under 35 U.S.C. 154(b) by 384 days.

(21) Appl. No.: 15/755,477

(22) PCT Filed: Aug. 16, 2016

(86) PCT No.: PCT/US2016/047126
§ 371 (c)(1),
(2) Date: Feb. 26, 2018

(87) PCT Pub. No.: WO2017/040021
PCT Pub. Date: Mar. 9, 2017

(65) Prior Publication Data
US 2018/0169308 A1 Jun. 21, 2018

Related U.S. Application Data

(60) Provisional application No. 62/212,997, filed on Sep. 1, 2015.

(51) Int. Cl.
*A61M 1/00* (2006.01)

(52) U.S. Cl.
CPC .......... *A61M 1/0003* (2013.01); *A61M 1/007* (2014.02); *A61M 1/0011* (2013.01); *A61M 1/0015* (2014.02); *A61M 1/0088* (2013.01); *A61M 2205/8281* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,278,089 A | * | 7/1981 | Huck | A61M 1/0011 604/134 |
| 4,397,643 A | * | 8/1983 | Rygiel | A61M 1/0015 215/11.3 |
| 4,578,060 A | * | 3/1986 | Huck | A61M 1/0011 604/133 |

(Continued)

*Primary Examiner* — Guy K Townsend

(57) ABSTRACT

Disclosed herein are devices and methods for reduced pressure tissue therapy. Some variations of suction devices for reduced pressure tissue therapy comprise a housing, a suction force generating mechanism located within the housing, and a storage module configured to retain tissue exudates. In some variations, the storage module includes a sleeve configured to collect tissue exudates. The sleeve may include a support element to help maintain the lateral structural integrity of the sleeve and/or retain the cross-sectional geometry of the sleeve under negative pressure. In use, the storage module may reduce sanitary and/or biohazard risks by preventing the exudates from contacting the housing and/or suction force generating mechanism. The storage module is configured to be replaced so that the housing and suction force generating mechanism can be used for more than one session.

32 Claims, 16 Drawing Sheets

(56) References Cited

U.S. PATENT DOCUMENTS

| | | | |
|---|---|---|---|
| 8,007,257 B2* | 8/2011 | Heaton | A61M 1/0025 417/472 |
| 8,128,607 B2* | 3/2012 | Hu | A61M 1/0009 604/313 |
| 8,162,908 B2* | 4/2012 | Hu | A61M 1/0086 604/313 |
| 8,177,764 B2* | 5/2012 | Hu | A61M 1/0086 604/313 |
| 8,337,474 B2* | 12/2012 | Hu | A61M 1/0086 604/313 |
| 8,641,692 B2* | 2/2014 | Tout | A61M 1/0011 604/316 |
| 8,679,079 B2* | 3/2014 | Heaton | A61M 3/0262 604/313 |
| 8,728,045 B2* | 5/2014 | Hu | A61M 1/0072 604/319 |
| 8,728,046 B2* | 5/2014 | Hu | A61M 1/007 604/319 |
| 8,753,322 B2* | 6/2014 | Hu | A61M 1/0066 604/319 |
| 8,795,246 B2* | 8/2014 | Hu | A61M 1/0066 604/319 |
| 8,858,516 B2* | 10/2014 | Hu | A61M 1/0068 604/290 |
| 8,926,575 B2* | 1/2015 | Hu | A61M 1/0086 604/313 |
| 8,961,481 B2* | 2/2015 | Hu | F16L 37/36 604/313 |
| 9,283,307 B2* | 3/2016 | Hu | F16L 37/36 604/319 |
| 9,561,312 B2* | 2/2017 | Heaton | A61M 1/0088 604/321 |
| 9,579,430 B2* | 2/2017 | Hu | A61M 1/0096 604/319 |
| 9,895,471 B2* | 2/2018 | Hu | A61M 1/007 604/319 |
| 9,943,629 B2* | 4/2018 | Hu | A61M 1/0066 604/321 |
| 10,265,441 B2* | 4/2019 | Coulthard | A61M 1/0088 604/321 |
| 10,314,954 B2* | 6/2019 | Hu | A61M 1/0096 604/319 |
| 10,398,808 B2* | 9/2019 | Heaton | A61M 1/0088 604/321 |
| 2004/0111015 A1* | 6/2004 | Ladd | A61M 1/0015 600/300 |
| 2008/0108977 A1* | 5/2008 | Heaton | A61M 1/0011 604/543 |
| 2010/0042021 A1* | 2/2010 | Hu | F16L 37/36 601/6 |
| 2010/0160901 A1* | 6/2010 | Hu | A61M 1/0088 604/543 |
| 2010/0198173 A1* | 8/2010 | Hu | A61M 1/0009 604/319 |
| 2010/0198174 A1* | 8/2010 | Hu | F16L 37/36 604/319 |
| 2010/0228205 A1* | 9/2010 | Hu | A61M 1/0072 604/319 |
| 2011/0130691 A1* | 6/2011 | Hu | A61M 1/007 601/6 |
| 2011/0295220 A1* | 12/2011 | Heaton | A61M 1/0049 604/319 |
| 2012/0022475 A1* | 1/2012 | Hu | A61M 1/0009 604/319 |
| 2012/0071845 A1* | 3/2012 | Hu | A61M 1/007 604/319 |
| 2012/0078207 A1* | 3/2012 | Hu | F16L 37/36 604/319 |
| 2012/0083754 A1* | 4/2012 | Hu | A61M 1/007 604/319 |
| 2012/0191053 A1* | 7/2012 | Hu | A61M 1/007 604/319 |
| 2012/0209225 A1* | 8/2012 | Hu | A61M 1/0096 604/319 |
| 2013/0006204 A1* | 1/2013 | Hu | A61M 1/0009 604/319 |
| 2014/0155849 A1* | 6/2014 | Heaton | A61M 39/24 604/321 |
| 2014/0243767 A1* | 8/2014 | Hu | A61M 1/0088 604/319 |
| 2014/0276488 A1* | 9/2014 | Locke | A61M 1/0015 604/319 |
| 2014/0276498 A1* | 9/2014 | Connor | A61M 1/0088 604/321 |
| 2015/0025486 A1* | 1/2015 | Hu | A61M 1/0068 604/319 |
| 2015/0148761 A1* | 5/2015 | Hu | A61M 1/007 604/319 |
| 2017/0100525 A1* | 4/2017 | Heaton | A61M 1/0025 604/321 |
| 2017/0128641 A1* | 5/2017 | Hu | A61M 1/0066 604/319 |
| 2018/0169308 A1* | 6/2018 | Hu | A61M 1/007 604/319 |
| 2018/0177925 A1* | 6/2018 | Hu | A61M 1/007 604/319 |
| 2018/0250453 A1* | 9/2018 | Hu | A61M 1/0068 604/321 |
| 2019/0298899 A1* | 10/2019 | Hu | A61M 1/0066 604/321 |

* cited by examiner

REDUCED PRESSURE TISSUE THERAPY DEVICE

RELATED APPLICATIONS

This application claims the benefit, under 35 USC 119(e), of the filing of U.S. Provisional Patent Application No. 62/212,997 entitled "Reduced Pressure Tissue Therapy Device," filed Sep. 1, 2015, which is incorporated herein by reference for all purposes.

BACKGROUND

Research has shown that applying reduced pressure to a tissue wound may provide several beneficial effects. For example, applying sub-atmospheric pressure to a wound may lead to retraction of the damaged tissue edges and thus may expedite healing by facilitating wound contraction. Reduced pressure wound therapy may also provide mechanical stimulation to the damaged tissue, which may release growth factors to the wound bed to promote healing. In some cases, applying suction to a wound may remove necrotic tissue from the wound bed and may help to reduce bacterial load. The application of reduced pressure may increase blood flow to the damaged tissue, which may expedite healing. In addition, reduced pressure may remove granulation inhibiting metalloproteinase enzymes, which may enhance tissue remodeling and healing.

In light of these and other benefits of reduced pressure tissue therapy, methods and devices that ensure a reliable application of reduced pressure to a wound may be desirable.

BRIEF SUMMARY

In the art, it is known to apply negative pressure wound therapy using self-contained devices comprising a chamber and piston seal. As these devices are designed to be single-use, after therapy is delivered and the chamber is filled with wound exudates, the entire device is meant to be subsequently disposed of. However, due to cost restrictions and care settings, for example, there may be instances when it may be desirable to reuse the device. Reusing the device may involve purging the chamber of collected wound exudates, but this practice may pose sanitary and possibly biohazard risks. Because the exudates may comprise foul odors and may contain infectious microorganisms, purging the chamber may aerosolize the exudates and residue may remain inside the chamber, flow paths or the exterior of the device. Disclosed herein are negative pressure wound therapy devices designed to minimize biohazard contamination. The devices may comprise a durable, reusable component and a disposable, replaceable component.

Existing reduced pressure systems are known to include bellows, wherein negative pressure created in the bellows draws in fluids and tissue exudates to facilitate wound healing. Examples of systems employing bellows are disclosed in U.S. Pat. Nos. 4,578,060, 4,278,089, 8,641,692, and 8,007,257, which are hereby incorporated by reference in their entirety. A disadvantage of these and other typical negative pressure systems is when a vacuum is generated within the bellows, the negative pressure may urge the bellows to collapse laterally inwardly, and/or reduce or otherwise alter the cross-sectional geometry of the bellows. If the cross-section of the bellows fully collapses and closes due to the generated suction, the therapeutic negative pressure will no longer be transmitted to the intended delivery site. This may reduce the ability of the suction device to provide negative pressure by reducing the time or magnitude of the negative pressure that may be provided to a tissue site. Disclosed herein are negative pressure wound therapy devices having a sleeve which may comprise a support element to help maintain the lateral structural integrity of the sleeve and/or retain the cross-sectional geometry of the sleeve under negative pressure.

One variation of a reduced pressure therapy device may comprise a housing comprising a force generating mechanism, a distal port, and a storage module. The storage module may comprise a sleeve in fluid communication with the distal port, where the sleeve may have a wall and a support element along the wall configured to resist inward collapse of the wall under negative pressure. A proximal end wall of the sleeve may be attached to the suction force generating mechanism. The wall of the sleeve may be flexible and the support element may comprise a support structure that is more rigid than the flexible wall. In some variations, the support structure may comprise a helical coil, one or more rings or loops, wire grid scaffolding, a mesh or weave, and/or any like structures. The support element may comprise hinges, and the hinges may comprise living hinges or may comprise mechanical hinges that have discrete components that are pivotally connected by a connecting structure. Mechanical hinges may comprise engaging structures that lock the hinge in a desired maximum open angle and/or interfering features that limit the maximum angle to which the hinge can open. In some variations, the wall of the sleeve may comprise a plurality of first pleats, where each first pleat is perpendicular to a longitudinal axis of the device and defines a first angle. The support element may be located along at least one first pleat, and may optionally comprise a second material added to the sleeve wall at the first pleat, where the second material defines a second pleat having a second angle more acute than the first angle. For example, the support element may comprise a second material extending from the first pleat and protruding perpendicularly to a longitudinal axis of the sleeve for a distance between about 0.005 inches and about 0.02 inches, e.g., between about 0.01 inches and about 0.015 inches.

The support structure may be enclosed within the wall of the sleeve, or located on an inner surface of the wall of the sleeve, or located on an outer surface of the wall of the sleeve, or located on an inner surface and an outer surface of the wall of the sleeve. In some variations, the sleeve may further comprise a distal valve, which may be a one-way valve. The suction force generating mechanism may comprise a force member, where the force member may comprise a constant or variable force spring. The device may also comprise a sliding assembly translatable along the longitudinal axis of the housing. In some variations, the sliding assembly may be a sliding seal assembly or may be attached to the suction force generating mechanism. The proximal end wall of the sleeve may be attached to the sliding assembly by snap-fit, screw-fit, twist-fit, friction-fit, adhesives, hooks and loop engagement, magnetic engagement, clips, and/or clasps. The device may optionally comprise an activation tool configured to urge the sliding assembly distally along a longitudinal axis of the housing. In some variations, the sleeve of the device may be detachable from the suction force generating mechanism and the distal port. The sleeve wall may comprise a film or membrane.

BRIEF DESCRIPTION OF THE DRAWINGS

FIG. 2D shows one variation including fins; FIG. 2E shows another variation including additional material protruding from the hinge.

FIG. 3A depicts the device in an opened configuration with the storage module detached from the housing and the sleeve in a collapsed state; FIG. 3B depicts the storage module attached to the housing and the device in a partially depleted configuration; FIG. 3C depicts the device in a depleted state and with the storage module detached from the housing.

DETAILED DESCRIPTION

Figure 1A:
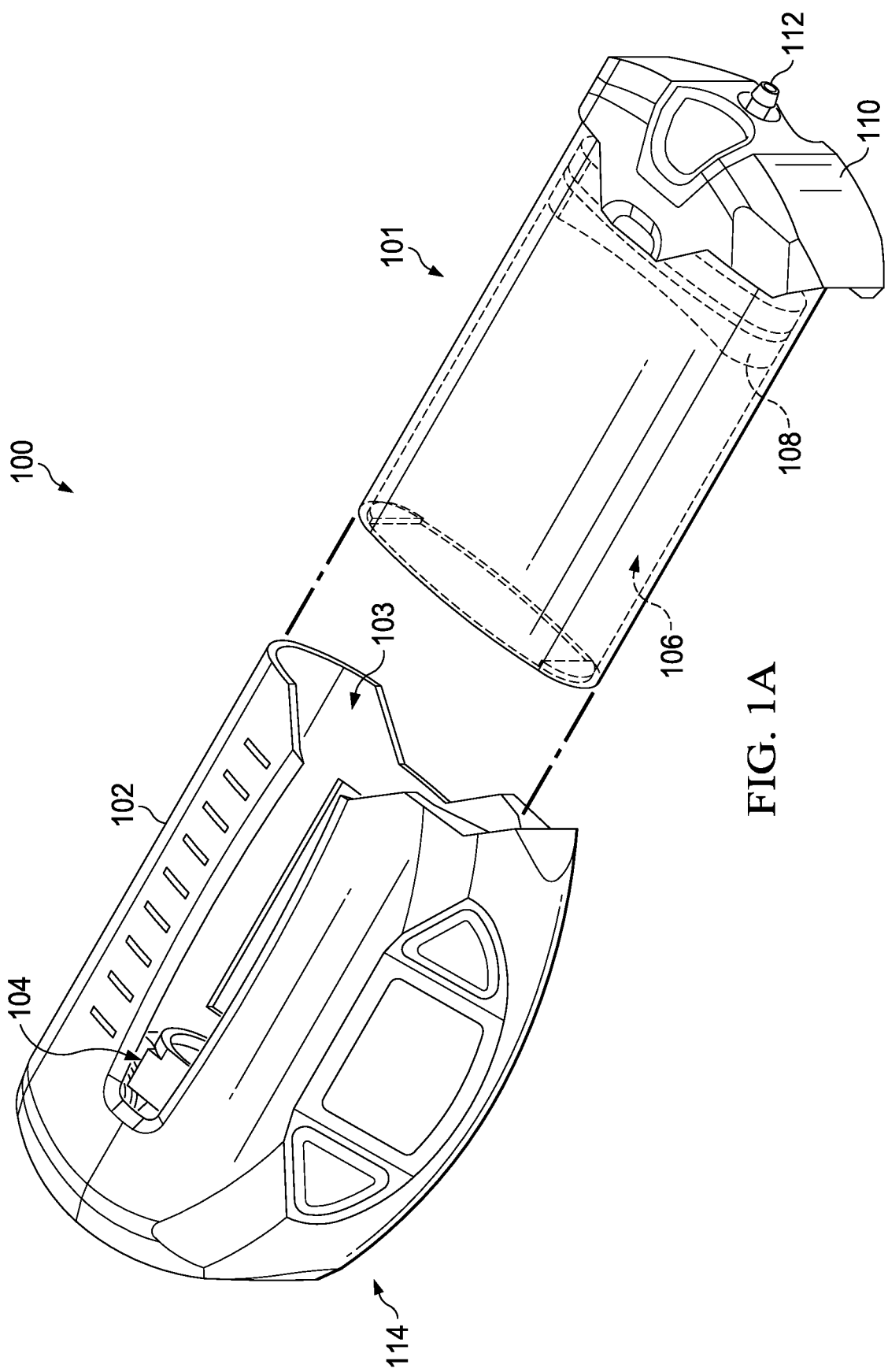
FIG. 1A is a perspective component view of a variation of a suction device comprising a detachable exudate storage module and a housing.

Described herein are devices and methods for reduced pressure tissue therapy. Suction devices for reduced pressure tissue therapy may be configured to remove and/or store tissue exudates. Exudates are typically body fluids or mixed fluids and other cellular matter. In some variations, suction devices may comprise a durable or reusable component and a disposable component configured to reliably attach to the durable or reusable component. For example, suction devices for reduced pressure tissue therapy may comprise a housing, a suction force generating mechanism that creates negative pressure, and a detachable exudate storage module configured to segregate or isolate collected tissue exudates. In some variations, the housing may be reused (without re-sterilization or other refurbishing), while the suction force generating mechanism and/or exudate storage module may be replaced with each treatment. In other variations, both the housing and the suction force generating mechanism may be reused and the exudate storage module replaced, while in still other variations, the housing, suction force generating mechanism, and exudate storage module may be replaced after each treatment. This may help reduce biohazard contamination of the reusable portions of a suction device. The detachable storage module may comprise a chamber for the collection and sequestering of exudates. While the reduced pressure therapy devices described herein may be characterized as having a durable portion (e.g., the housing, suction force generating mechanism, etc.) and a single-use portion that retains and/or sequesters tissue exudates (e.g., a detachable exudate storage module), other variations of suction devices may not comprise any components that can be re-used. Such suction devices may need to be entirely replaced after a single therapy session.

The detachable exudate storage module of a suction device may be removed when the suction device is depleted and/or when a certain amount of exudates has been collected. In some embodiments, the storage module may comprise a fluid retention assembly to resist or prevent leakage of the exudates that have been suctioned into the storage module. In some variations, the storage module may comprise a suction chamber and a sleeve within the suction chamber such that exudates that are collected by the suction device are retained by the sleeve and do not contact the inner wall of the suction chamber. The sleeve may be semi-permeable (e.g., permeable to air, but not to liquid) or impermeable (e.g., impermeable to both air and liquid). Alternatively or additionally, the detachable storage module may comprise a suction chamber and a distal cap of a suction device. Some storage modules may also comprise a sliding assembly movably disposed in the suction chamber. In some variations, the sliding assembly is a sliding seal assembly. The storage module may comprise the sleeve without a suction chamber, or alternatively, the sleeve may be used with a suction chamber (e.g., inside a suction chamber). Any type of fluid collection compartment may be included with the detachable storage module of a suction device so that accumulated tissue exudates may be removed without contaminating the other components of the suction device and/or the patient. Examples of suction devices for reduced pressure tissue therapy with various types of detachable exudate storage modules are described below.

Some variations of detachable exudate storage modules may comprise a sleeve having flexible and/or resilient walls. However, due to the flexibility and/or resiliency of the sleeve walls, the suction chamber may collapse inwardly when negative pressure is generated therein. This may limit the amount of negative pressure that can be generated by a suction chamber of a particular size/volume. Optionally, a sleeve having flexible walls may comprise a support structure that may help maintain cross-sectional patency of the suction chamber under negative pressure conditions. In some variations, the support structure that is stiffer and/or more rigid than the walls. In some variations, the sleeve may comprise a plurality of folds or pleats (e.g., accordion folds, bellows folds) along the sleeve walls, and a support structure having a plurality of loops or rings each located along a fold or pleat. The looped support structure may form an outline that corresponds to the cross-sectional shape of the suction chamber. In another variation, a sleeve may comprise flexible and/or resilient walls that do not have pre-formed folds or creases. For example, the sleeve may be made of a film or membrane. A support structure that is more rigid and/or stiffer than the film or membrane may wrap around the sleeve (e.g., on the inner and/or outer surface of the sleeve walls) to help prevent inward collapse of the sleeve during the generation of negative pressure. For example, the support structure may be a coil (e.g., a helical coil) that circumscribes around the sleeve along its length. Some flexible and/or resilient sleeves may not have any support structure(s), but may be attached to the suction chamber in such a way as to prevent the sleeve from collapsing inwardly under negative pressure conditions. For example, the sleeve may comprise a material that at least partially adheres to the wall of the suction chamber. Alternatively or additionally, the sleeve may comprise a material that is permeable to air but not to liquids or solids, which may allow for the generation of negative pressure and collection of exudates while maintaining cross-sectional patency in the presence of negative pressure. In still other variations, the sleeve may comprise walls that are rigid enough to withstand forces that may cause the walls to collapse inwardly. For example, the sleeve may comprise a series of wall segments that are attached to each other by movable junctions (e.g., hinges) such that the segments are capable of being folded onto each other (e.g., to prime the device) and of being unfolded (e.g., to generate and apply negative pressure). In such variations, the movable junctions may be configured to retain cross-sectional geometry of the sleeve. Alternatively or additionally, the sleeve may comprise bellows that have an overall tapered or conical geometry, such as nested bellows.

Figure 1B:
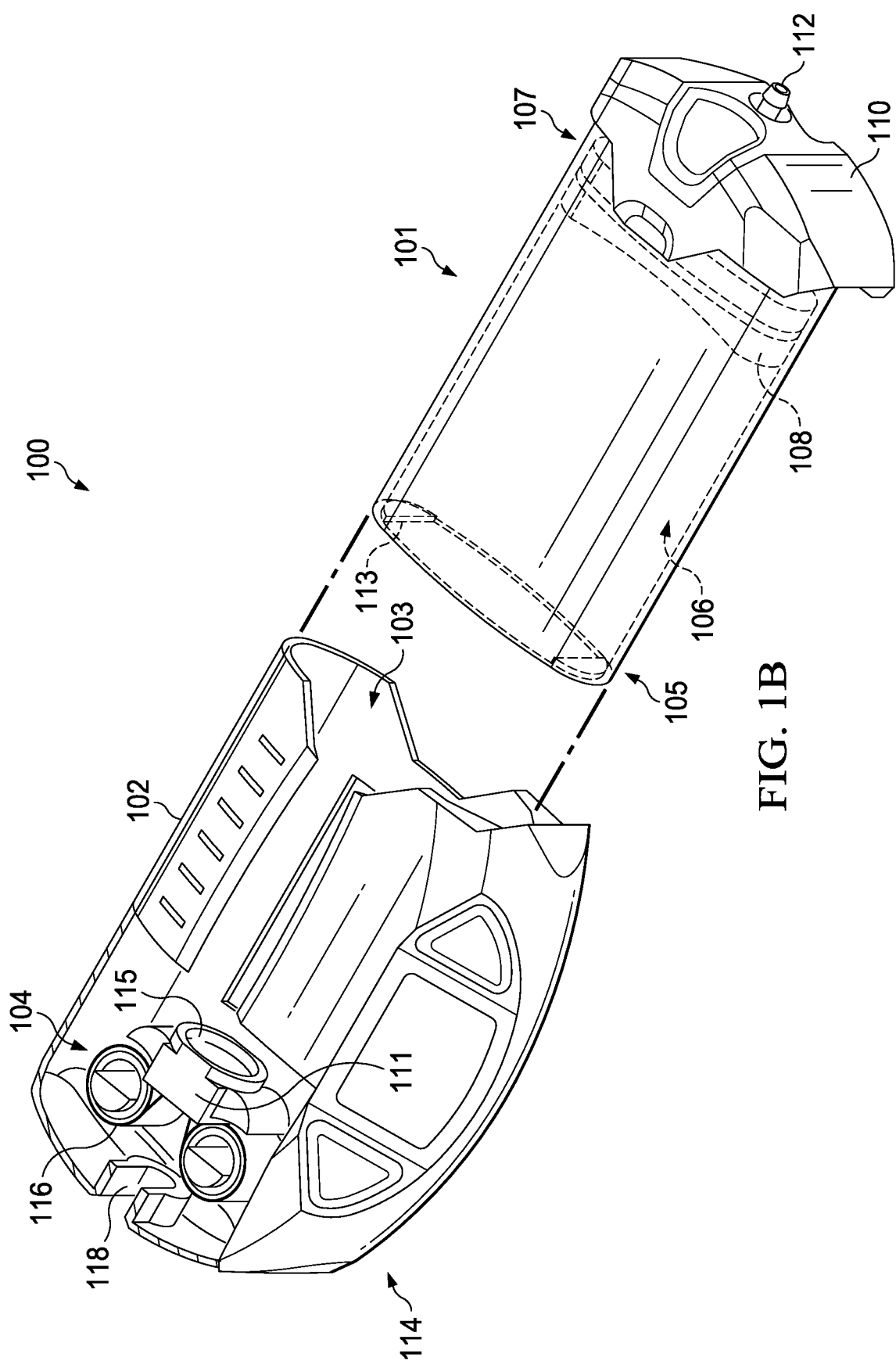
FIGS. 1B and 1C are perspective cutaway views of the device in FIG. 1A with the storage module uncoupled and coupled to the housing, respectively.
Figure 1C:
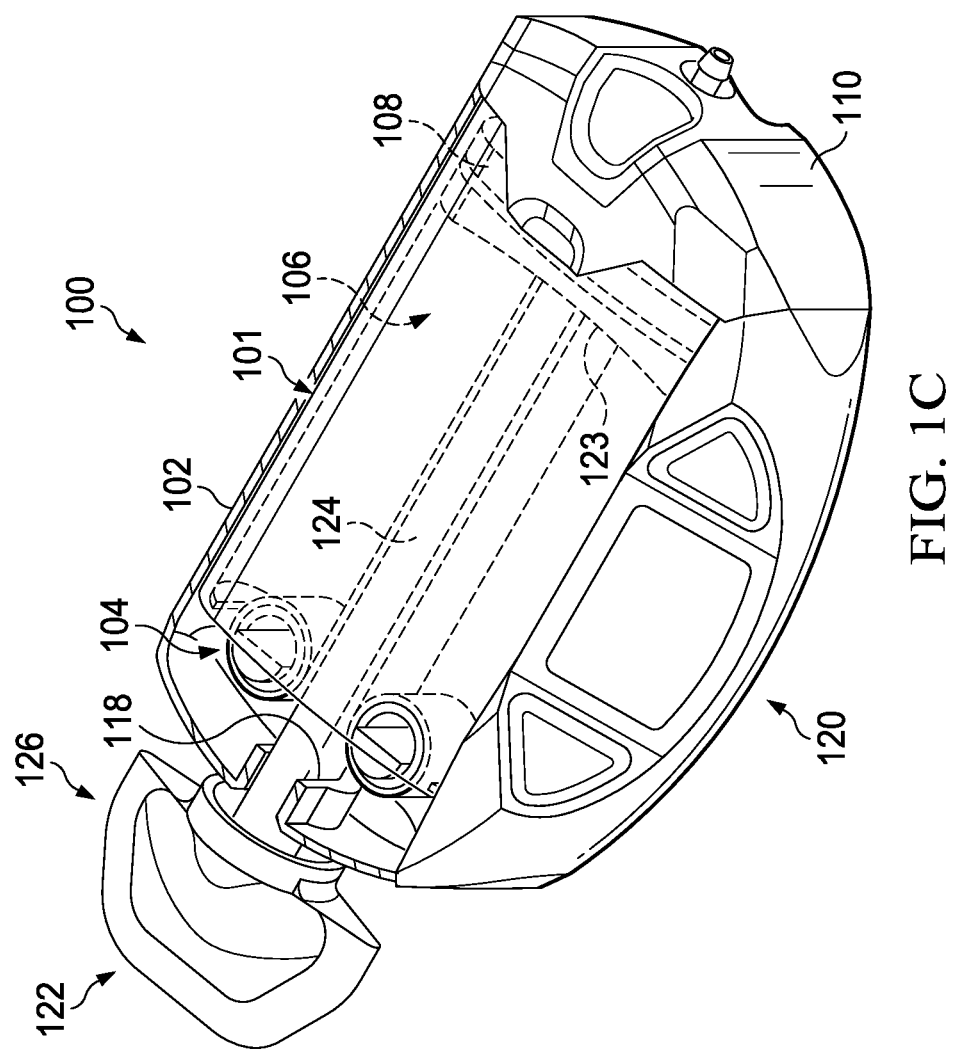

Some variations of detachable exudate storage modules may comprise a rigid suction chamber without a sleeve configured to sequester exudates that may be collected in the course of negative pressure therapy. For example, a suction device may comprise a housing, a suction force generating mechanism, and a detachable storage module comprising a rigid suction chamber. The suction force generating mechanism may create negative pressure in the suction chamber, and the suction chamber may be configured to collect and sequester exudates. One example of such a suction device that may be used for reduced pressure tissue therapy is depicted in FIGS. 1A-1C. Suction device 100 comprises a housing 102, a suction force generating mechanism 104 at a proximal portion 114 of the housing 102, and a storage module 101 configured to be releasably retained within a cavity 103 of the housing 102. The storage module 101 may comprise a suction chamber 106, a sliding seal assembly 108 movable within the suction chamber 106, and a distal cap 110 attached at a distal end of the suction chamber 106. The sliding seal assembly 108 is concentrically disposed within the suction chamber 106 and is adapted to create an airtight separation between the portion of the suction device 100 below it and the remainder of the suction device 100. The sliding seal assembly 108 is configured to longitudinally traverse between a proximal end 105 and a distal end 107 of the suction chamber 106 while maintaining a substantially airtight seal. The distal cap 110 may comprise a port 112 that is in fluid connection with the suction chamber 106. The port may be configured to connect to a tubing that is connected to a dressing assembly at the tissue site such that there is fluid communication between the dressing assembly and the internal volume of the suction chamber. The housing 102 and suction chamber 106 may comprise a translucent or optically clear material, or an opaque material with or without a translucent or optically clear window. The housing 102 may optionally comprise indicia to provide a reference for the position of the sliding seal assembly within the suction chamber during the course of reduced pressure therapy.

FIG. 1B is a partial cutaway view of the suction device 100. The suction force generating mechanism 104 may comprise one or more springs 116 that are attached at their proximal ends to housing 102 using posts or pins, for example, and releasably attached at their distal ends to the sliding seal assembly 108 of the storage module 101. The springs 116 may be constant force springs, but in other variations may be variable force springs, including springs wherein force generated in an extended position is lower than the force generated in a retracted position. The constant force springs 116 may be extended when the suction device 100 is in a charged configuration (i.e., capable of applying negative pressure) and coiled when the suction device 100 is in a depleted configuration (i.e., no longer able to apply negative pressure). Extending the springs 116 may generate potential energy within the springs that may be used to exert a proximally-directed force on the sliding seal assembly, thereby creating negative pressure within the portion of the suction chamber below the sliding seal assembly. Other types of springs that are capable of applying a proximally directed force on the sliding seal assembly may also be used.

The suction force generating mechanism 104 may be releasably attached to the storage module 101 by any suitable mechanism, for example, by snap-fit, screw-fit, twist-fit, friction-fit, adhesives, hooks and loops, clips, clasps, clamps, and the like. In some variations, the suction force generating mechanism is attached to the sliding seal assembly such that activating the suction force generating mechanism (i.e., releasing the potential energy from within the springs as they reassume a coiled configuration) may urge the sliding seal assembly proximally to generate negative pressure in the suction chamber.

In some variations, the springs 116 are directly and releasably attached to the sliding seal assembly 108. In other variations, the distal end of the springs 116 may be attached to a spring block 111, and the spring block may be releasably attached to the sliding seal assembly 108 of the storage module 101. For example, the spring block 111 may have a connector 115 that is configured to releasably attach to a connector (not shown) on the sliding seal assembly 108. The attachment between the spring block 111 and the sliding seal assembly 108 may be any suitable releasable attachment mechanism, such as snap-fit, screw-fit, twist-fit, friction-fit, adhesives, hooks and loop engagement, magnetic engagement, clips, clasps, and the like. Any releasable attachment mechanism that is configured to provide controllable and repeatable engagement and disengagement between the spring block and the sliding seal assembly may be used. Additional attachment mechanisms are described below.

FIG. 1C depicts a partial cutaway view of the suction device 100 with the storage module 101 inserted into the housing 102 and the sliding seal assembly 108 moved from a proximal position to a distal position near the distal end 107 of the suction chamber 106 by an activation tool 122. The activation tool 122 may be used to mechanically charge the suction device 100 by extending the springs 116 so that negative pressure may be generated within the suction chamber 106. The housing 102 may comprise an aperture 118 that is sized and shaped for the insertion of an elongate body portion 124 of the activation tool 122 therethrough. A distal end of the elongate body portion 124 122 may be pushed against a proximal surface 123 of the spring block 111, which may in turn urge the sliding seal assembly 108 distally to charge the suction device 100. As shown in FIG. 1C, a portion of the suction force generating mechanism 104 may reside in the storage module 101 during use (e.g. when springs 116 are in the maximally extended position). The activation tool 122 may be pushed until the sliding seal assembly 108 contacts a wall of the distal cap 110, until the sliding seal assembly 108 is adjacent the distal end wall of the suction chamber 106, until the springs 116 are maximally extended, and/or until mechanical interference between an enlarged head portion 126 of the activation tool 122 and the proximal portion 114 of the housing 102 resist further insertion. Other variations of suction devices that may be used for reduced pressure therapy, as well as methods of using suction devices, are described in pending U.S. patent application Ser. No. 12/372,661 (now U.S. Pat. No. 8,177, 764), filed on Feb. 17, 2009, which is hereby incorporated by reference in its entirety and included in the Appendix.

In some variations, the spring block 111 may comprise an alignment mechanism (not shown) to help guide the spring block 111 as it is urged by the activation tool 122 such that the spring block connector 115 is substantially aligned with a connector on the sliding seal assembly 108. For example, the spring block may comprise one or more weak magnets and the sliding seal assembly may comprise one or more corresponding weak magnets of the opposite polarity. As the spring block is moved by the activation tool into close proximity to the sliding seal assembly, the weak magnets may attract each other, which may help the user align the connectors of the spring block and the sliding seal assembly. Optionally, the one or more magnets in the sliding seal assembly may allow the position of the sliding seal assembly within the suction chamber to be detected by an alarm system, as described below. In other examples, the device may comprise a sliding seal assembly with a coupling structure with tapered sides or alignment surface that are configured to initially receive a protrusion of the spring block connector and guide the spring block connector toward an aligned final position as the spring block connector is pushed further against the sliding seal assembly. The coupling structure may comprise a recess or opening. Of course, in other variations, the sliding seal assembly may comprise a protrusion and the spring block connector may comprise a recess or opening with tapered sides. Additionally or alternatively, the sliding seal assembly may comprise longitudinally extending alignment rails along which the activation tool may be moved to help ensure the activation tool urges the spring block connector to the connector on the sliding seal assembly. The alignment rails may comprise grooves or protrusions along their longitudinal axes that may correspond to protrusions or grooves on the activation tool and/or spring block connector to help prevent lateral deviation as they are advanced towards the sliding seal assembly.

Once the connectors of the spring block and the sliding seal assembly are aligned, the releasable attachment mechanism may be activated to attach them together. In some variations, contacting the spring block and sliding seal assembly may cause them to be engaged. For example, the spring block and sliding seal assembly may automatically engage by a latch mechanism or a magnetic mechanism. Alternatively or additionally, the attachment mechanism may be activated by rotating, twisting, sliding, pushing, etc. the activation tool 122. In some variations, twisting the activation tool 122 in first direction may activate the attachment mechanism such that the spring block is engaged with the sliding seal assembly. Twisting the activation tool 122 in a second direction may deactivate the attachment mechanism and disengage the spring block from the sliding seal assembly. In some variations, the connector on the spring block may have mechanical structures that fit with complementary structures on the connector of the sliding seal assembly. For example, as depicted in FIG. 1B, the connector 115 may be threaded, and may correspond to a threaded connector on the sliding seal assembly 108. Twisting the activation tool 122 may engage the threaded structures of the spring block 111 and the sliding seal assembly 108. In some variations, the attachment mechanism may be configured to automatically disengage the spring block and the sliding seal assembly when the suction device is substantially or fully depleted (e.g., the sliding seal assembly has moved from a distal location in the suction device to a proximal location in the suction device, a certain quantity of exudates has been collected). Other examples of attachment mechanisms between the suction force generating mechanism and a portion of the storage module (e.g., the sliding seal assembly, suction chamber, etc.) are described below.

While the storage module 101 may be attached to the suction device housing 102 by engaging the sliding seal assembly 108 with the spring block 111 as described above, alternatively or additionally, the storage module 101 may be attached to the housing 102 by a mechanical engagement between the suction chamber 106 and the housing 102. For example, the suction chamber 106 may comprise a ledge 113 along a rim of the proximal end 105 that may engage a protrusion or hook in the housing 102 (e.g., by snap-locking). The ledge 113 may also help prevent the sliding seal assembly 108 from sliding proximally out of the suction chamber 106 so that the sliding seal assembly acts as a barrier between exudates collected in the suction chamber and the remainder of the suction device. Alternatively or additionally, the side walls of the suction chamber 106 may comprise one or more grooves or protrusions that may correspond to protrusions or grooves along the walls of the housing 102, such that sliding the suction chamber 106 into the cavity 103 may align these grooves and protrusions to securely retain the storage module 101 within the housing 102. In some variations, a proximal portion of the storage module may comprise a deflectable hooked protrusion that is configured to engage a tab on the suction device housing such that the storage module and the housing may be snap-locked together. Examples of other releasable attachment mechanisms between the storage module and the housing of a suction device may include screw-fit, twist-fit, friction-fit, adhesives, clips, clasps, hook and loop engagement, magnetic engagement, and the like. In some variations, the distal cap 110 may be similarly configured to releasably engage a distal portion of the housing 102.

The suction devices described herein may optionally comprise an alarm system that is configured to sense the state of the suction device and to provide an alert to a user (e.g., to let the user know when the suction device is depleted and may need to be replaced or recharged). For example, an alarm system 120 may be located on the suction device housing 102, and may be configured to detect the location of the sliding seal assembly 108 within the suction chamber 106 of the storage module 101. The alarm system may generate an alert (e.g., visual, audio, tactile, electronic, etc.) when the suction device is depleted. The alarm system 120 may comprise one or more buttons that may allow a user to control the function of the suction device, as well as a display to provide visual feedback to the user. In some variations, the detection mechanism of the alarm system may comprise a reed switch located in the housing of the suction device that is configured to sense the location of a magnetic component that may be located in the sliding seal assembly. In some variations, the storage module may comprise a pressure transducer that may be probed by circuitry in the housing. The circuitry may read the pressure transducer and provide an alert as to the status of the suction chamber, and whether it needs to be removed and/or replaced. In some embodiments, the alarm system may be located on an attachment device (e.g., clip, strap, etc.) that is configured to retain a suction device. When the ability of the suction device to generate negative pressure is depleted, the storage module may be removed from the attachment device and replaced with a new storage module to resume negative pressure therapy. In other variations, the entire suction device may be removed and replaced, as may be desirable. Variations of alarm systems, sensing mechanisms, and attachment devices are described in U.S. patent application Ser. No. 13/175,744 (now U.S. Pat. No. 8,795,246), filed on Jul. 1, 2011, which is hereby incorporated by reference in its entirety and included in the Appendix.

Figure 1D:
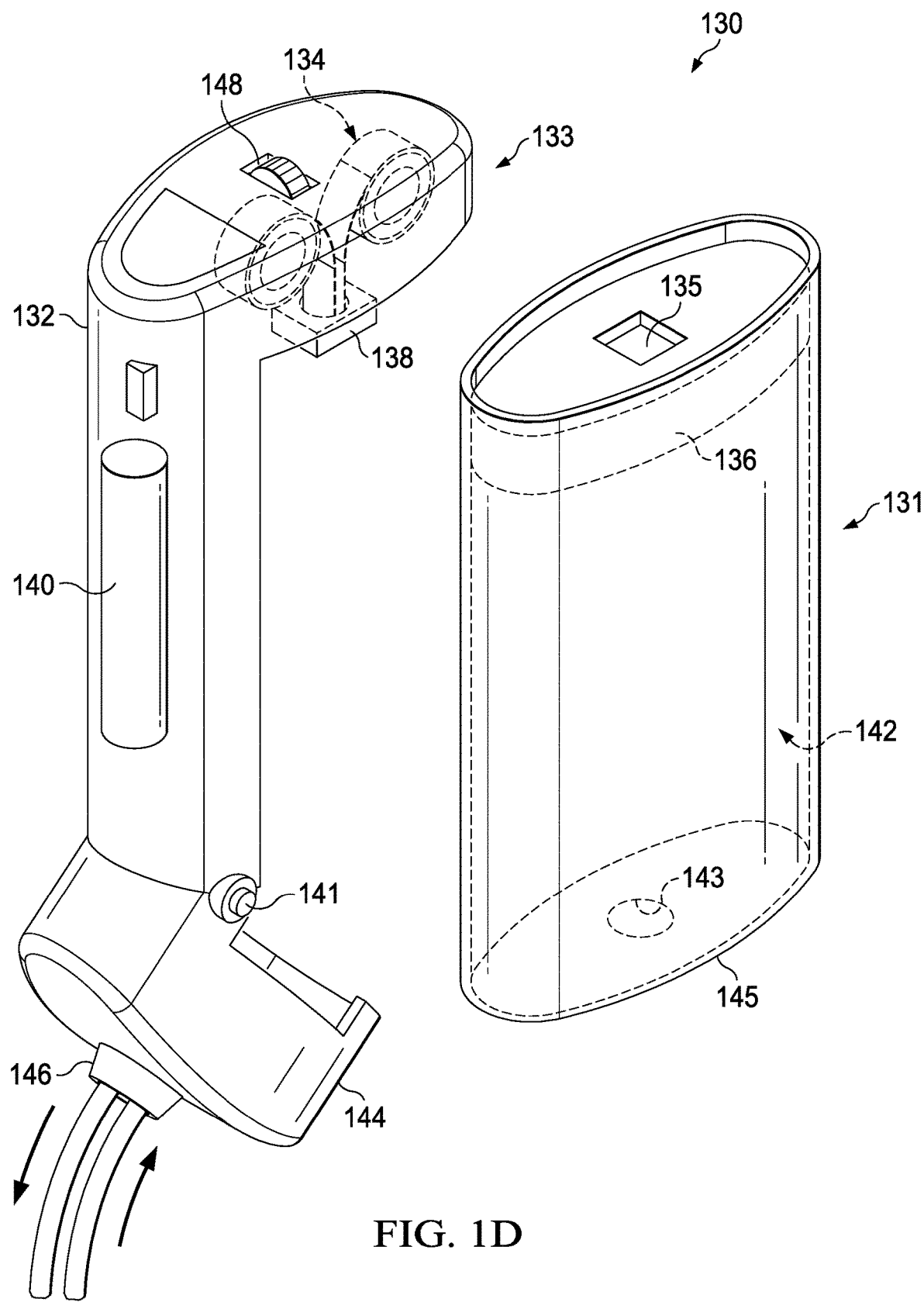
FIG. 1D is a perspective view of another variation of a suction device comprising a detachable storage module and a rotatable retention bracket.

Sensing mechanisms may also be used to control the negative pressure that is generated in the suction chamber, and may be used to activate or deactivate the suction force generating mechanism to generate more negative pressure. For example, the sensing mechanisms may detect the pressure in the suction chamber and compare it to a target pressure level. A controller of the alarm system may adjust the suction force generating mechanism to attain the desire pressured target. The pressure in the suction chamber may be adjusted in various ways, for example, by providing a slight rotational oscillation to the springs (e.g., constant force springs) or linear oscillation of the sliding seal assembly. These adjustments may be performed by attaching a gear mechanism to the bearings that retain the springs and connecting the gear mechanism to an electrical motor. Alternatively, retraction of the springs in contact with a roller (i.e., the axis around which the springs are wound) can modulate the transmitted spring force by modifying the curvature of the extended spring. Varying the roller shape can modulate the spring force and negative pressure produced. In other variations, the adjustments in pressure in the suction chamber may be performed by attaching the sliding seal assembly to a line and pulley system that is connected to an electric motor. Power for the motor may be provided by a battery contained within the housing of the suction device. While a storage module of a suction device may be installed into the housing by sliding it into a cavity of the housing, in some embodiments, the storage module of a suction device may be engaged with the housing in an alternate way. One variation of a suction device that may comprise a detachable storage module configured to be engaged to the suction device using a hinged mechanism is depicted in FIG. 1D. Suction device 130 may comprise a housing 132, a suction force generating mechanism 134 located at a proximal portion 133 of the suction device, and a storage module 131 configured to be releasably retained by the distal bracket 144. The distal bracket 144 may contact a distal portion of the storage module 131 to press it against a proximal portion 133 of the housing 132. The housing 132 may comprise an aperture 148 at the proximal end for the insertion of an activation tool therethrough. The distal bracket 144 may be attached to the housing 132 by a pivot or hinge 141. The distal bracket 144 may comprise a bracket port 146 that may be configured to align with a port 143 of the storage module 131. The storage module 131 may comprise a rigid suction chamber 142 and a sliding seal assembly 136 movable within the suction chamber. The port 143 may be located at a distal end of the suction chamber 142. The suction device 130 may also comprise an alarm system 140 as previously described. The storage module 131 may be releasably attached to the housing 132 by a detachable mechanical interfit between the sliding seal assembly and the suction force generating mechanism. Alternatively, the suction force generating mechanism 134 may be coupled to a spring block 138, and the spring block 138 may be configured to releasably attach to the sliding seal assembly 136 to help retain the storage module 131 within the housing 132. The releasable attachment mechanism may be any of the previously described attachment mechanisms, and may be capable of controllable and repeatable engagement and disengagement of the spring block and the sliding seal assembly. Once the spring block 138 is engaged with the sliding seal assembly 136, the distal bracket 144 may be rotated around the hinge 141 such that the bracket port 146 on the distal bracket may be aligned with the port 143 of the suction chamber. This may form a continuous fluid conduit from the bracket port 146 to the suction chamber port 143 and into the suction chamber 142. When the storage module 131 is installed in the housing 132, and the length of the bracket abuts and supports the distal surface 145 of the storage module, the distal bracket 144 may form a substantially right angle with respect to a longitudinal portion of the housing 132. The force with which the distal bracket 144 presses the storage module 131 may be sufficient to enable a sufficiently airtight seal such that the suction force generating mechanism 134 may create negative pressure within the suction chamber 142. The hinge 141 may be locked such that it is no longer rotatable. Optionally, the storage module may be attached to the housing using the attachment mechanisms described above, including screw-fit, twist-fit, friction-fit, adhesives, clips, clasps, hook and loop engagement, magnetic engagement, and the like. For example, the bracket 144 may snap-fit with the distal surface 145 of the storage module, and/or the spring block 138 may snap-fit with the connector 135 of the sliding seal assembly. The proximal rim of the suction chamber 142 may have a ledge that interfits with a tab, protrusion or hook of the housing 132 (e.g., by snap-locking). There may also be corresponding grooves, protrusions, etc. along the lengths of the suction chamber wall and the housing wall such that the grooves and protrusions releasably engage to retain the storage module 131 within the housing 132 during reduced pressure therapy. After the suction device is depleted, the hinge 141 may be unlocked, the distal bracket rotated, and the storage module removed and replaced.

Figure 2A:
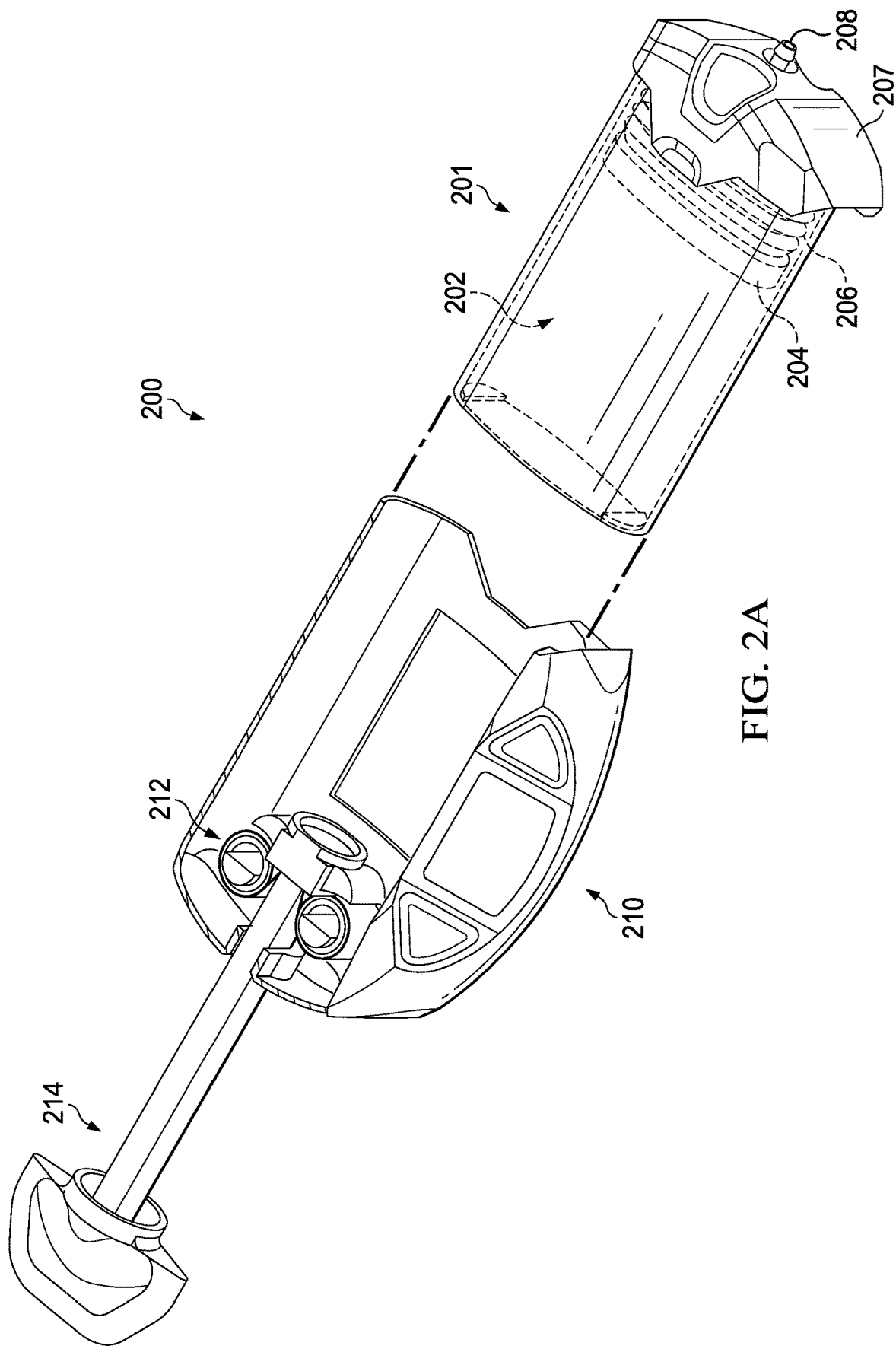
FIG. 2A is a perspective cutaway view of one variation of a reduced pressure therapy device comprising a detachable storage module and sleeve in a compressed configuration.
Figure 2B:
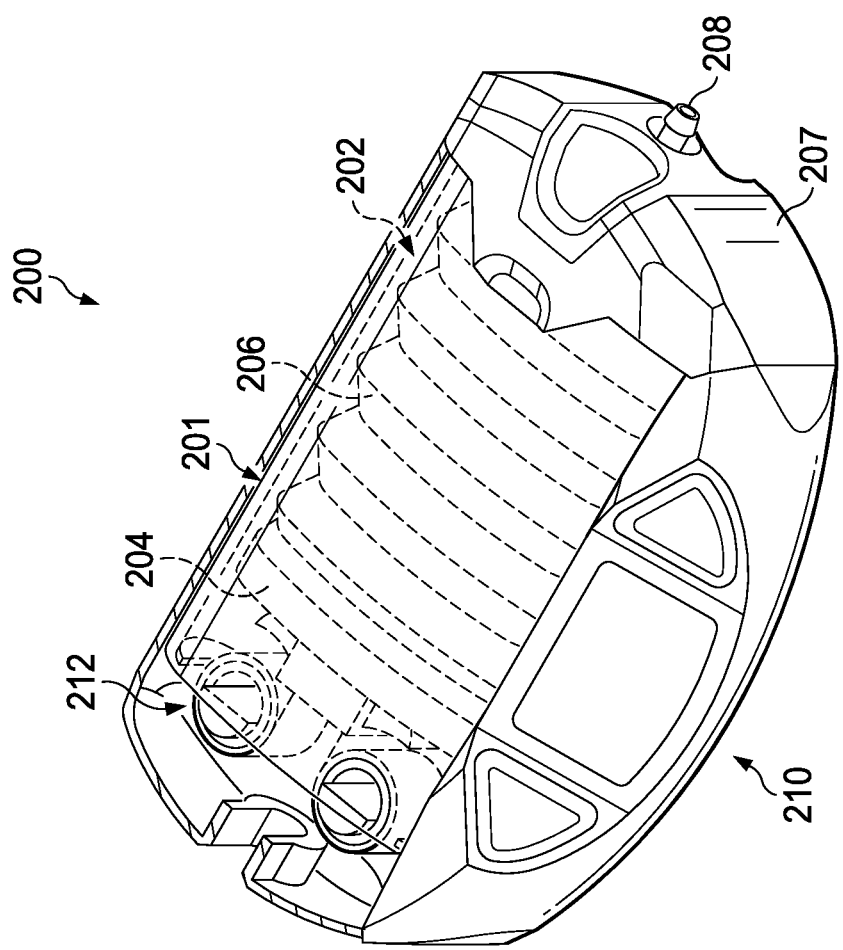
FIG. 2B is a partial cutaway view of the device of FIG. 2A with the sleeve in an expanded configuration.
Figure 2C:
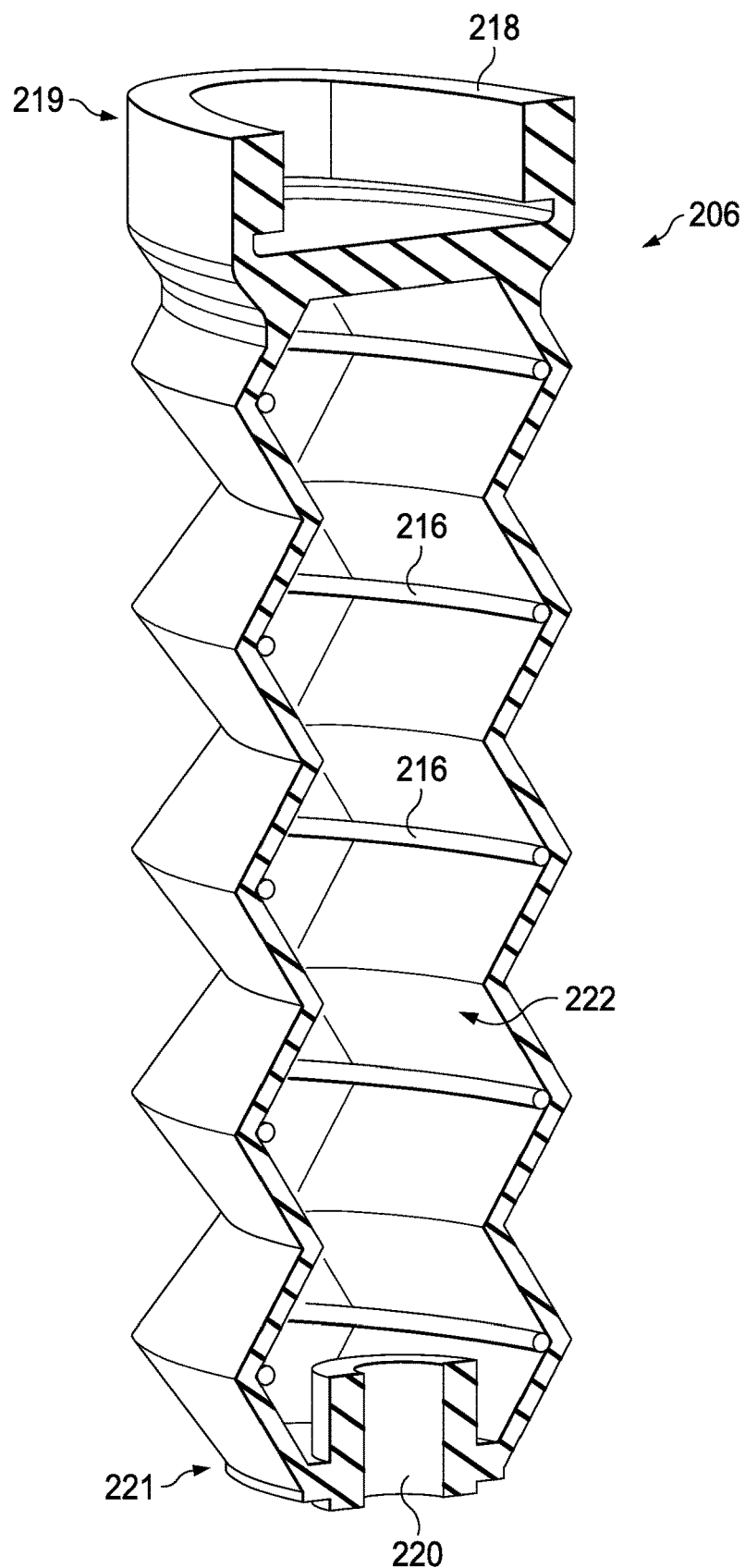
FIG. 2C is a perspective cross-sectional view of the sleeve used in FIGS. 2A and 2B having structural supports.

In some variations, a suction device may have a storage module that comprises a suction chamber and a sleeve within the chamber. For example, a detachable exudate storage module may comprise a suction chamber, a sliding assembly movable along the length of the suction chamber, a port at a distal portion of the chamber, and a sleeve interposed between the sliding assembly and the port. One variation of such a suction device is depicted in FIGS. 2A-2C. Suction device 200 comprises housing 210, a suction force generating mechanism 212 at the proximal portion of the housing, and a detachable exudate storage module 201. The storage module 201 may comprise a suction chamber 202, a sliding assembly 204, a distal cap 207 with a distal port 208, and a sleeve 206 interposed between the sliding assembly 204 and the port 208. The sleeve 206 may be a pouch comprising a closed proximal end wall and an internal compartment. The sliding assembly 204 is not required to provide a seal with the suction chamber 202 to create an airtight separation between the portion of the suction device below it and the remainder of the suction device. The sliding assembly 204 attaches to or interfaces with the flexible sleeve to alter the volume of the internal compartment. In some variations, the proximal portion of sleeve 206 may be releasably or non-releasably attached to the sliding assembly 204 and the distal portion of sleeve 206 may be attached to the distal cap 207 such that the internal compartment of sleeve 206 is in fluid communication with the distal port 208. In other variations, the sleeve 206 may not be attached to sliding assembly 204. The sleeve may be provided in a collapsed state that is folded and configured to longitudinally expand easily within the suction chamber without interfering with the sliding assembly. The volume of the internal compartment of the sleeve may be adjusted by moving the sliding assembly 204 proximally or distally along the length of the suction chamber 202. In the course of reduced pressure therapy, tissue exudates may be collected through the distal port 208 into the sleeve 206. The sleeve 206 may act as a barrier between the tissue exudates and the walls of the suction chamber to prevent contamination of the suction chamber by the exudates. The sleeve 206 may be made of a semi-permeable material (e.g., permeable to air, but not liquid) or an impermeable material (e.g., impermeable to both air and liquid). For example, the sleeve 206 may be made of a compliant material such as polyvinyl chloride, low density polyethylene, polyurethane, silicone rubber, thermoplastic elastomers (TPEs), other rubber compositions and the like. The thickness of the sleeve may be in the range of about 0.01 inch or less, sometimes less than about 0.001 inch. In some variations, the surfaces between the sleeve and the internal wall of the suction chamber may be treated with talc or other substance to reduce frictional resistance as the sleeve expands or unfolds.

In some variations, the sleeve 206 may have pre-formed creases. FIG. 2A depicts the sleeve 206 in a compressed configuration, where the sleeve folds along pre-formed creases. When the storage module 201 is installed in the housing 210, an activation tool 214 may be used to releasably attach the suction force generating mechanism 212 to the sliding assembly 204 and to urge the sliding assembly 204 distally into a charged configuration (e.g., using any of the releasable attachment mechanisms described above). In some variations, the suction force generating mechanism may comprise one or more force members (e.g., constant force springs), which may be attached approximately at the midline of the sliding assembly/sleeve, while in other variations, the force members may be attached along the sides of the sliding assembly/sleeve. For example, a suction force generating mechanism may comprise two constant force springs, and a first spring may be attached to the left side of the sliding assembly/sleeve and the second spring may be symmetrically attached to the right side of the sliding assembly/sleeve. Urging the sliding assembly 204 distally may act to longitudinally compress the sleeve 206, which may reduce the volume of the internal compartment of the sleeve and generate potential energy in the springs of the suction force generating mechanism 212 for generating negative pressure. The activation tool 214 may be removed after the suction device 200 is placed in the charged configuration. Activating the suction force generating mechanism 212 (e.g., releasing the potential energy from within the springs as they reassume a coiled configuration) may urge the sliding assembly 204 proximally, which may generate negative pressure in the sleeve 206 and draw tissue exudates therein.

FIG. 2B depicts the suction device 200 in a depleted configuration, where the sleeve 206 is expanded, and may be filled with tissue exudates. When the suction device 200 is depleted, the storage module 201 may be disengaged from the suction force generating mechanism 212 and discarded. For example, the attachment between the sliding assembly 204 of the storage module 210 and the suction force generating mechanism 212 may be released using the activation tool 214 as previously described. Optionally, the sleeve 206 may comprise a one-way valve which may help to prevent outflow of exudates as the sleeve is disengaged from the housing and/or suction force generating mechanism and/or sliding assembly. In some variations, the sleeve 206 may be releasably attached to the distal cap 207, the port 208, and the sliding assembly 204 so that the sleeve may be removed and discarded. After the sleeve 206 is removed, a new sleeve may then be installed in the storage module 201 and inserted into the housing 210 for an additional session of reduced pressure therapy. In other variations, the sleeve may be non-releasably attached to the distal cap 207, port 208, and sliding assembly 204. In such a variation, the entire storage module 201 may be discarded and replaced.

The sleeve 206 may be made of any material that this sufficiently flexible so that the flexible sleeve may be transitioned from a longitudinally compressed configuration to a longitudinally uncompressed configuration. For example, sleeve 206 may be made of elastomeric polymers, such as silicone and the like. However, when a vacuum is generated within the sleeve, the negative pressure may urge the sleeve to collapse laterally inwardly, and/or reduce or otherwise alter the cross-sectional geometry of the sleeve. If the cross-section of the sleeve fully collapses and closes due to the generated suction, the therapeutic negative pressure will no longer be transmitted to the intended delivery site. This may reduce the ability of the suction device to provide negative pressure by reducing the time or magnitude of the negative pressure that may be provided to a tissue site. Some variations of the sleeve may comprise flexible but non-stretchable materials or materials with limited stretch. Examples of such materials may include, but are not limited to, silicone rubber, thermoplastic elastomers (TPEs), polyurethane rubbers, fiber-reinforced polyurethane film, and laminated nylon.

Alternatively or additionally, the sleeve may comprise at least one support element that may help to maintain the lateral structural integrity of the sleeve under negative pressure and/or retain the cross-sectional geometry of the sleeve. In variations wherein the sleeve comprises flexible and/or resilient walls, the sleeve may further comprise a support element in the form of a scaffold or support structure that is stiffer than the sleeve wall material. Examples of materials for the support element may include, for example, polyethylene terephthalate (PET), high density polyethylene (HDPE), polyvinyl chloride (PVC), low density polyethylene (LDPE), polypropylene (PP), polystyrene, acrylonitrile butadiene styrene (ABS), metals such as steel or aluminum that are sufficiently stiff to not collapse during generation of the negative pressure. The support structure may be co-molded with or later inserted into the flexible sleeve. FIG. 2C depicts a longitudinal cross-sectional view of the sleeve 206 with one variation of a scaffold or support structure that may help the sleeve maintain its structural integrity (e.g., reduce lateral compression to resist inward collapse, maintain cross-sectional patency of the sleeve). The sleeve 206 may comprise one or more support loops or retention rings 216 that may be located along the creases or folds of the sleeve, where the retention rings are stiffer or more rigid than the walls of the sleeve. The stiff retention rings 216 may act to support the structure of the sleeve by counteracting the inward force that may arise from generating negative pressure within the sleeve. The retention rings 216 may also help to maintain the cross-sectional geometry of the sleeve. In some variations, the retention rings may not be separate structures, but may be regions of stiffer material located along the pre-formed creases of the sleeve. The stiff retention rings 216 may be located at one or more of the convex or concave folds of the sleeve 206 or may be located at selected pre-formed creases of the sleeve (e.g., along every crease, every other crease, etc.). The retention rings may be individual, unconnected loops, or may be connected to each other (e.g., in a coil-like configuration, helical coil configuration, chain-link configuration, etc.). Retention rings may also be located along a substantially planar surface of the sleeve.

Alternatively or additionally, support elements in the form of hinges may be disposed at one or more of the convex or concave folds of the sleeve that may allow for both bending and retaining the cross-sectional geometry of the sleeve. The hinges may be living hinges made of a resilient material, or mechanical hinges comprising discrete components that are pivotally connected by connecting structure, such as a pin, to enable the sleeve to fold/unfold along the creases. For example, the walls of the sleeve may comprise rigid planar structures, where the folds of the sleeve are formed by a hinge that attaches one rigid planar structure to the next. The hinge may allow the rigid planar structures to pivot as the sleeve is longitudinally collapsed or expanded, while the rigid planar structure may help to reduce lateral compression of the sleeve. As a support element, the hinge may be configured to resist inward collapse of the sleeve upon generation of negative pressure within the sleeve. In some variations, the hinge may also be configured to pivot open to a limited maximum degree, such as for example, 90 degrees, 120 degrees, 150 degrees, or 180 degrees. By limiting the maximum opening degree, the hinge may be prevented from opening too far (e.g., flipping open to greater than 180 degrees) and allowing the sleeve to buckle inwardly. In some variations, interfering features may be included on the rigid components and/or the connecting structure (e.g., pin) to prevent rotation of the rigid components beyond a certain degree. The interfering features may include a tab or other extension or protrusion of material. In one example, tabs provided on the rigid components may interfere with tabs provided on the connecting structure when the hinge is opened to 150 degrees. In other variations, the hinge may include a ratchet structure or other structure with engaging features (e.g., hooks and loops, ridges and recesses) that lock when the hinge is opened to the desired maximum degree. These engaging features may also resist collapse or buckling through incremental locking of the sleeve at longitudinally expanded configurations.

Figure 2D:
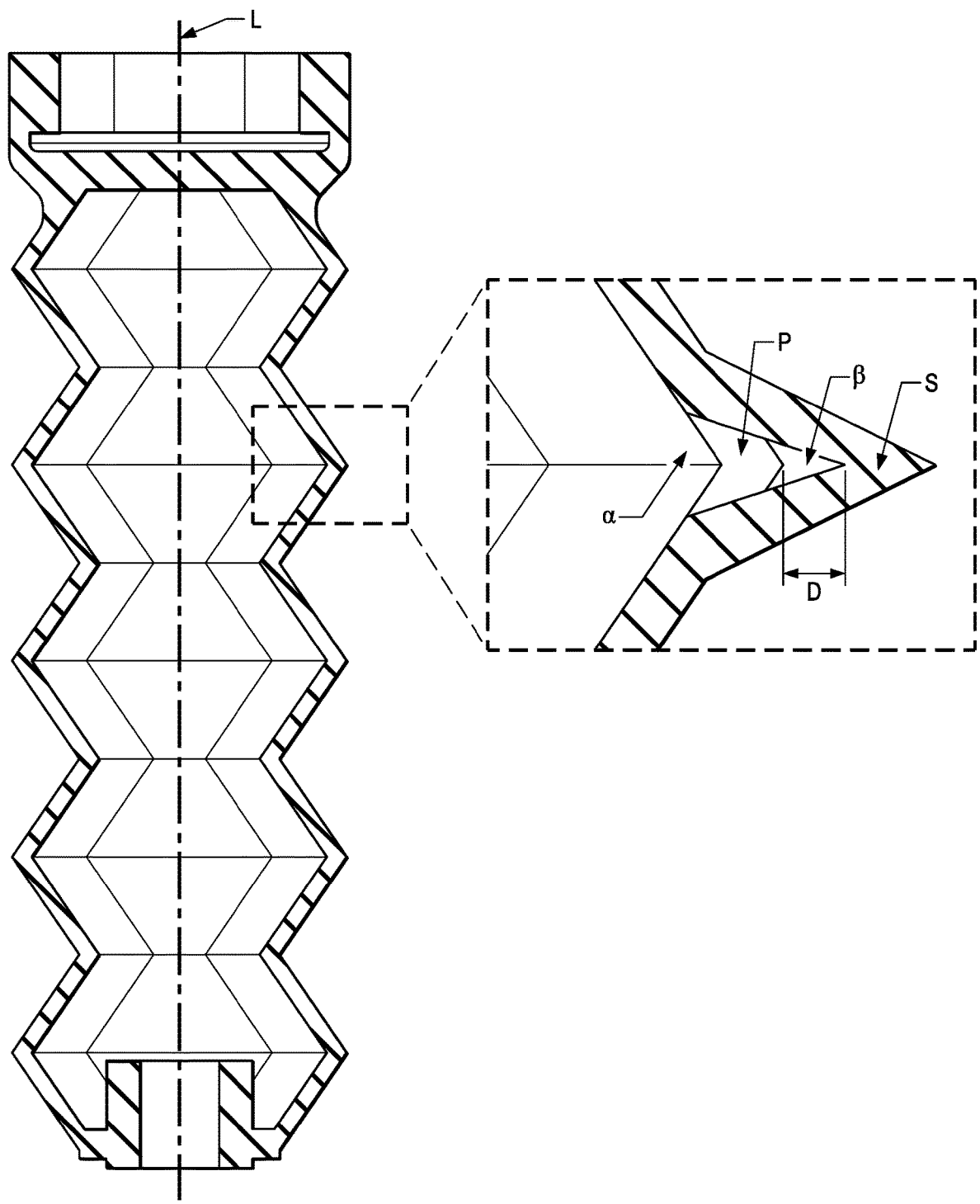
FIGS. 2D and 2E are enlarged cross-sectional views of variations of sleeves having hinges with modified geometries.

In some variations, the hinges may be reinforced with additional material, which may help provide additional structural integrity. In some of those variations, the additional material may modify the geometry of the sleeve at the hinge and decrease the angle to which the hinge is opened at the maximum expanded length of the sleeve. In one example shown in FIG. 2D, the hinge may comprise a primary wall P of the sleeve defining an angle α at a primary wall crease. The primary wall P defines a cross-sectional width W1 (not shown) of the sleeve as measured from the longitudinal axis L of the sleeve to and including the thickness of the primary wall P at the primary wall crease. A material forming a secondary wall S may be added to the hinge at a distance D from the primary wall crease to form a secondary wall crease. The secondary wall S defines a cross-sectional width W2 (not shown) of the sleeve as measured from the longitudinal axis L of the sleeve to and including the thickness of the secondary wall S at the secondary wall crease. W2 is equal to the sum of W1, distance D, and the thickness of secondary wall S. Secondary wall S defines an angle β at the secondary wall crease, wherein β is less than (e.g., more acute) than α. The greater cross-sectional width W2 and smaller angle β of secondary wall S decreases the angle to which the hinge will open when the sleeve is fully expanded or depleted, which may resist buckling throughout the range of negative pressures delivered. For example, a standard bellows may have a maximum angle opening of up to 150 degrees, or up to 170 degrees. Hinges configured with a secondary wall as described herein may have a maximum angle opening up to 90 degree, or up to 120 degrees. More generally, the structure/geometry and materials of the secondary wall may be selected to resist forces that may cause the sleeve or bellows to collapse inwardly.

Figure 2E:
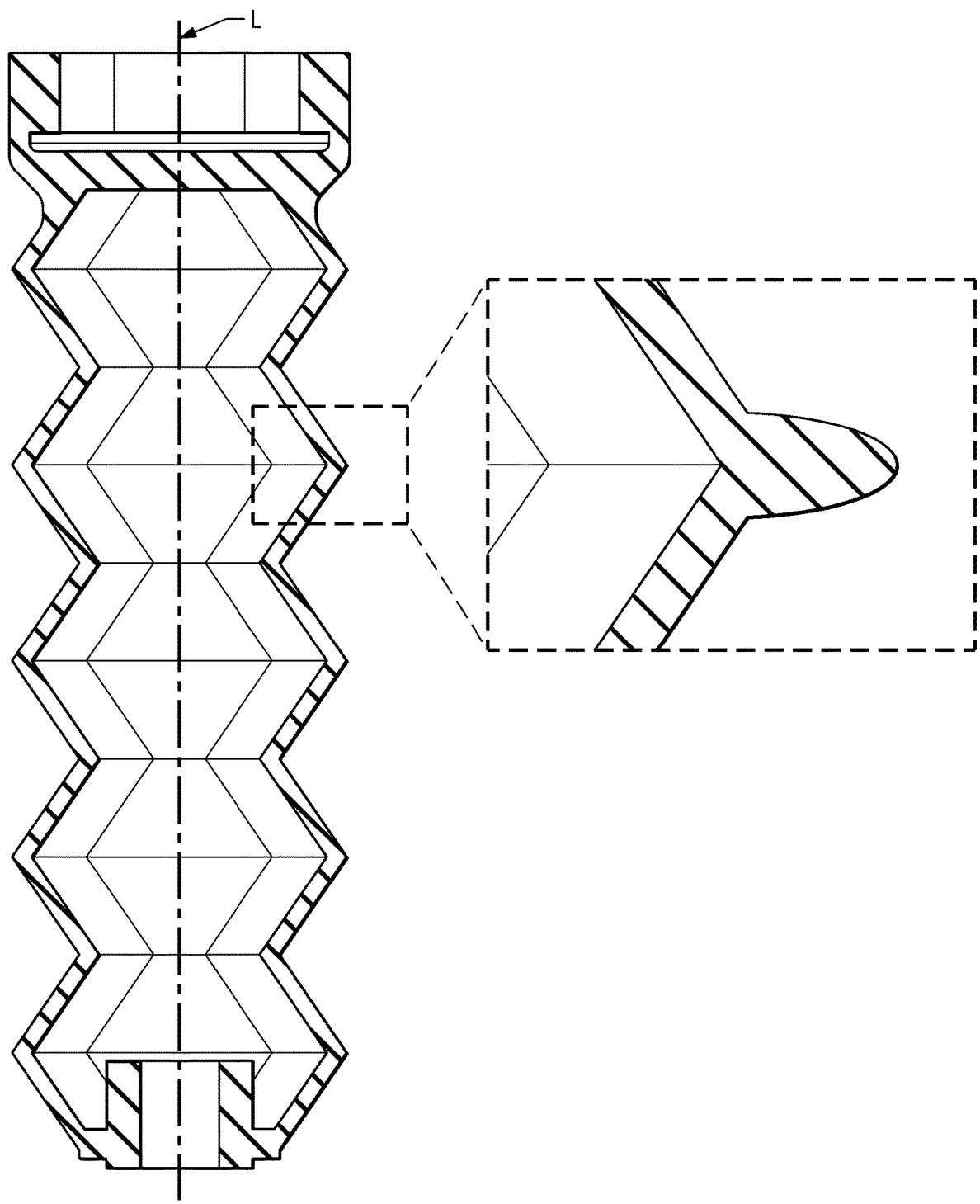

In another example shown in FIG. 2E, the hinge geometry is modified through the addition of material at the sleeve crease. The additional material may protrude from the hinge perpendicularly to the longitudinal axis of the sleeve such that the thickness of the hinge at the crease is increased by the thickness of the added material. The cross sectional width of the sleeve as measured from the longitudinal length L of the sleeve to and including the thickness of the sleeve wall will be increased by the thickness of the additional material. The additional material thickness may be such that it resists forces that may cause the sleeve or bellows to collapse, and may be between about 0.005 inches and about 0.02 inches, more specifically between about 0.01 inches and about 0.015 inches. Material of the specified thicknesses may be applied to living hinges, for example, to reinforce the hinge and help prevent inward buckling. In some variations, this additional material may be the same as the rest of the hinge or another different reinforcing material.

The sleeve 206 may also comprise connectors at its proximal end 219 and distal end 221 so that the sleeve may be attached to the sliding assembly and distal cap. The sleeve 206 may comprise a sliding assembly connector 218 at the proximal end, which may be sized and shaped to attach to the sliding assembly. For example, the connector 218 may comprise a recessed portion that corresponds to a protruding portion on the sliding assembly. The connector 218 may not be in fluid communication with the internal volume 222 of the sleeve, which may prevent any exudates that may be collected in the sleeve from contacting the sliding assembly. The sleeve 206 may also comprise a port connector 220 at the distal end 221, which may be sized and shaped to attach with the port 208 on the distal cap 207. For example, port connector 220 may be an aperture with a ledge that may be suitable for engaging with a barbed fitting on the port 208. The engagement between the port connector 220 and the port 208 may be any such that the lumen of the port 208 is in fluid connection with the connector 220 and the internal portion of the sleeve 206.

Figure 3A:
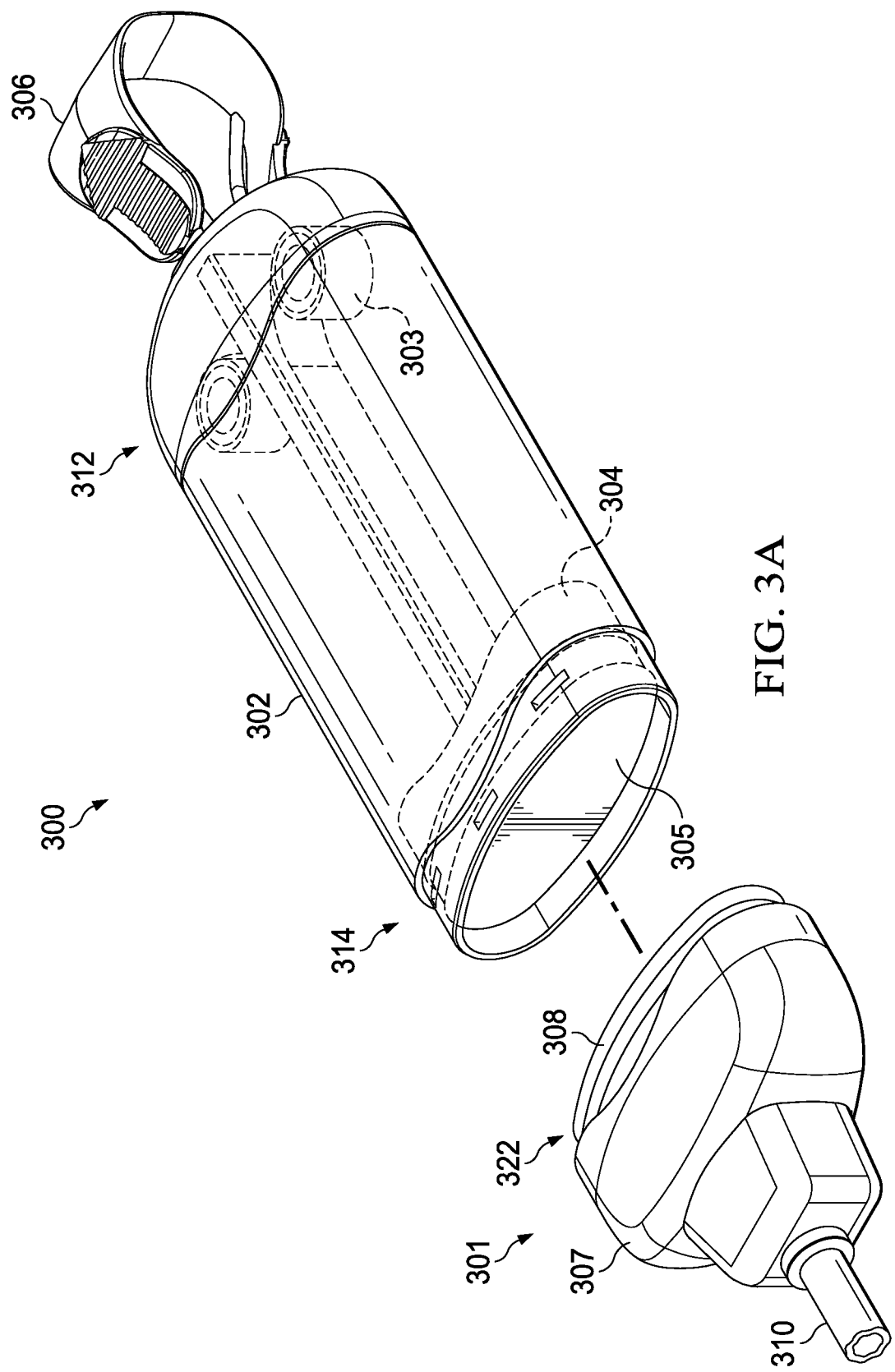
FIGS. 3A-3C are perspective views of another variation of a suction device comprising a housing and a detachable storage module with a sleeve.
Figure 3B:
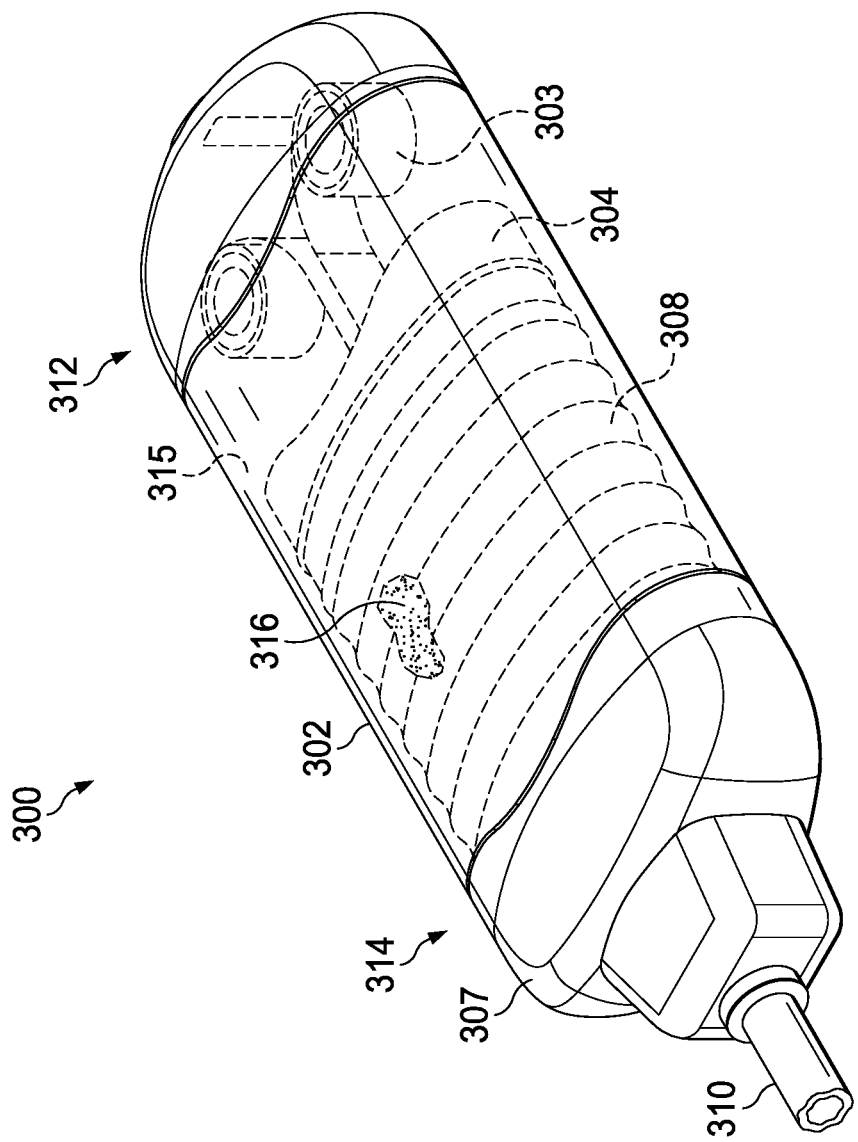
Figure 3C:
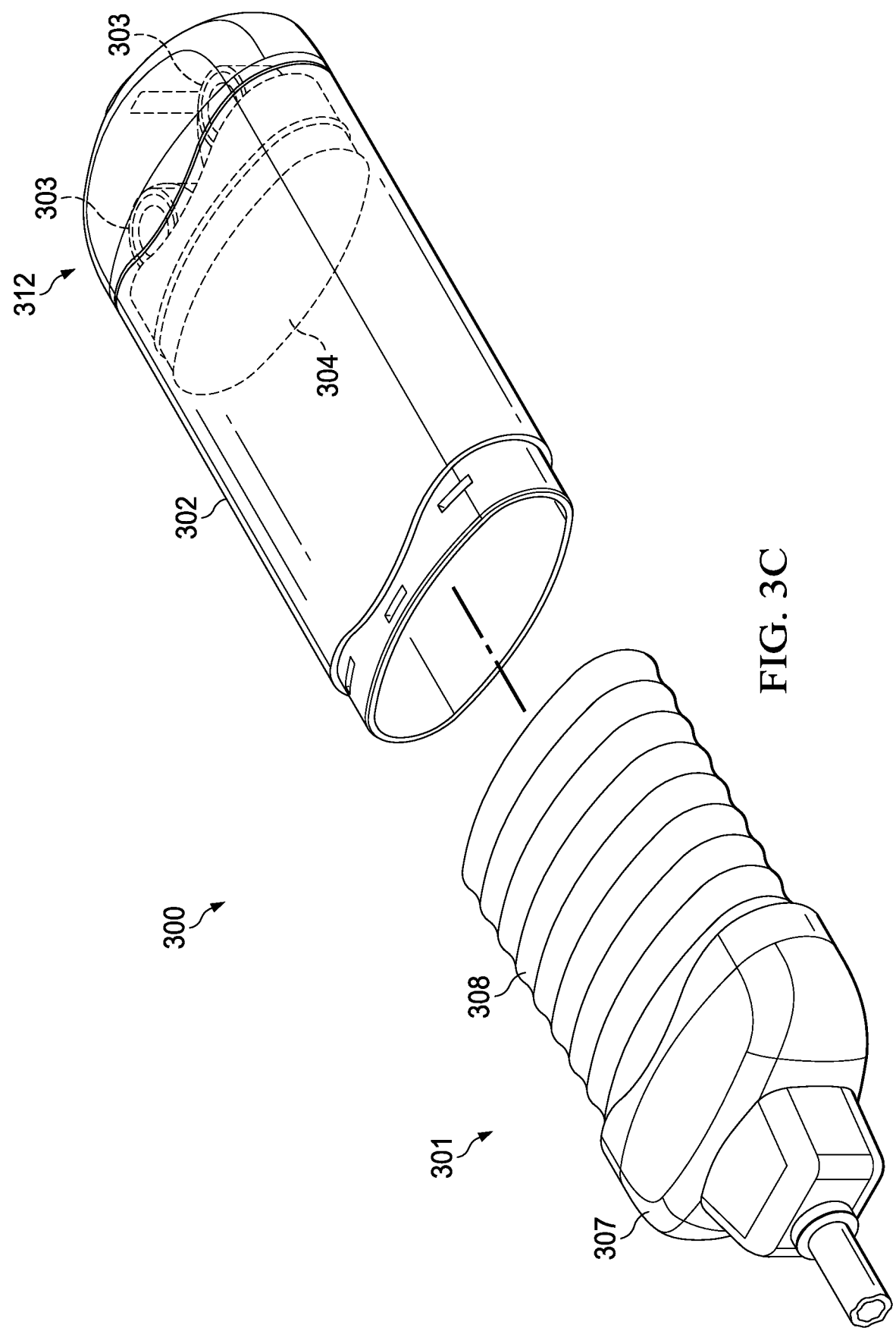

In some variations, a suction device may comprise a sleeve with a sliding seal assembly, as depicted in FIGS. 3A-3C. Suction device 300 may comprise a housing comprising a suction chamber 302, a sliding seal assembly 304 movable within the suction chamber 302 between a proximal portion 312 and a distal portion 314 of the suction device, and a suction force generating mechanism comprising constant force springs 303 attached to the sliding seal assembly 304. The suction device may further comprise an activation tool 306 and a storage module 301 configured to be attached at the distal portion 314 of the suction device. The storage module 301 may comprise a distal cap 307 and a sleeve 308 that may be in fluid connection with a tubing 310. The sleeve 308 may be a pouch comprising a closed proximal end wall and an internal compartment. The tubing 310 may transmit negative pressure generated in the sleeve and/or suction chamber to a downstream tissue region. The sleeve 308 may be releasably attached to the distal cap 307 using any of the attachment mechanisms previously described (e.g., using adhesives, clips, screws, hooks and loops, and the like). The volume of the internal compartment of the suction chamber and/or sleeve may be adjusted by moving the sliding seal assembly 304 proximally or distally along the length of the suction chamber 302. The sleeve may be provided in a collapsed state that is folded and configured to longitudinally expand easily within the suction chamber without interfering with the sliding seal assembly. The sleeve 308 may be made of any compliant semi-permeable or impermeable material, as described previously. Before the suction device 300 is used, the activation tool 306 may be used to urge the sliding seal assembly 304 to the distal portion 314 of the suction device, where a proximal portion of the sleeve 308 may or may not be releasably attached to the distal surface 305 of the sliding seal assembly 304. The distal cap 307 may be releasably attached to the suction chamber 302 by any suitable mechanism, as previously described, such that the flexible sleeve may be removed and replaced as often as may be desirable. The tubing 310 may be attached between the distal cap 307 and a dressing assembly for applying reduced pressure to a tissue region. In some variations, the suction device 300 may comprise a one-way valve configured to allow air to be released from the suction chamber, which may help prevent compression in the suction chamber when the distal cap 307 is attached at the distal portion 314.

FIG. 3B depicts the suction device 300 in a partially depleted configuration, where the constant force springs 303 have retracted the sliding seal assembly 304 proximally along at least a length of the suction chamber to generate negative pressure in the sleeve and/or suction chamber that may be transmitted to the tissue via the tubing 310. During reduced pressure therapy, exudates 316 may be captured in the sleeve 308. The sleeve 308 may act as a barrier between the exudates 316 and the internal walls 315 of the suction chamber 302 and/or the sliding seal assembly 304 such that the exudates do not contact with the walls of the suction chamber or the sliding sealing assembly. In some variations, the sleeve 308 may comprise a fluid retention assembly, which may increase the viscosity of the exudates and/or disinfect the exudates, as described below. The shape and volume of the sleeve may vary according to the quantity of exudates collected and the pressure gradient between the internal compartment of the sleeve and the suction chamber. For example, a sleeve may have a collapsed or longitudinally compressed configuration in the absence of exudates, and may longitudinally expand as the quantity of exudates collected increases. The constant force springs 303 may be able to generate negative pressure within a sleeve made of a material that is impermeable to both air and liquids. The negative pressure within the impermeable sleeve may result in a negative pressure gradient between the suction chamber and the internal compartment of the sleeve, thereby causing the sleeve to have a collapsed or compressed configuration in the absence of exudates. In some variations, the sleeve may be made of a material that is permeable to air but not to liquid (i.e., semi-permeable). Such a semi-permeable sleeve would reduce or prevent the formation of a negative pressure gradient between the suction chamber and the sleeve. Accordingly, the sleeve may not necessarily be collapsed or compressed in the absence of exudates, and in some variations, the internal compartment of the sleeve may occupy a substantial volume of the suction chamber in the absence of exudates. The accumulation of exudates in the course of negative pressure therapy may act to further expand the sleeve.

FIG. 3C depicts the suction device 300 after it has been depleted, and the storage module 301 has been detached from the suction chamber 302. In some variations, a suction device may be fully depleted when the sleeve is filled with exudates, while in other variations, a suction device may be fully depleted even when the flexible sleeve is not entirely filled with exudates. The storage module 301 may be removed from the suction chamber 302 by disengaging the distal cap 307 from the distal portion 314 of the suction chamber. This may release the attachment of the flexible sleeve 308 from the sliding seal assembly and/or internal walls of the suction chamber. The flexible sleeve 308 may be disposed after it has been removed from the distal cap 307. A new sleeve may be installed on the distal cap 307 and may be inserted into the suction device 300 as previously described to carry out an additional session of reduced pressure therapy. In some variations, the sleeve is non-releasably attached to the distal cap 307 (i.e., the sleeve may not be separated from the distal cap without tearing the sleeve), and both the sleeve and distal cap may be replaced.

Figure 3D:
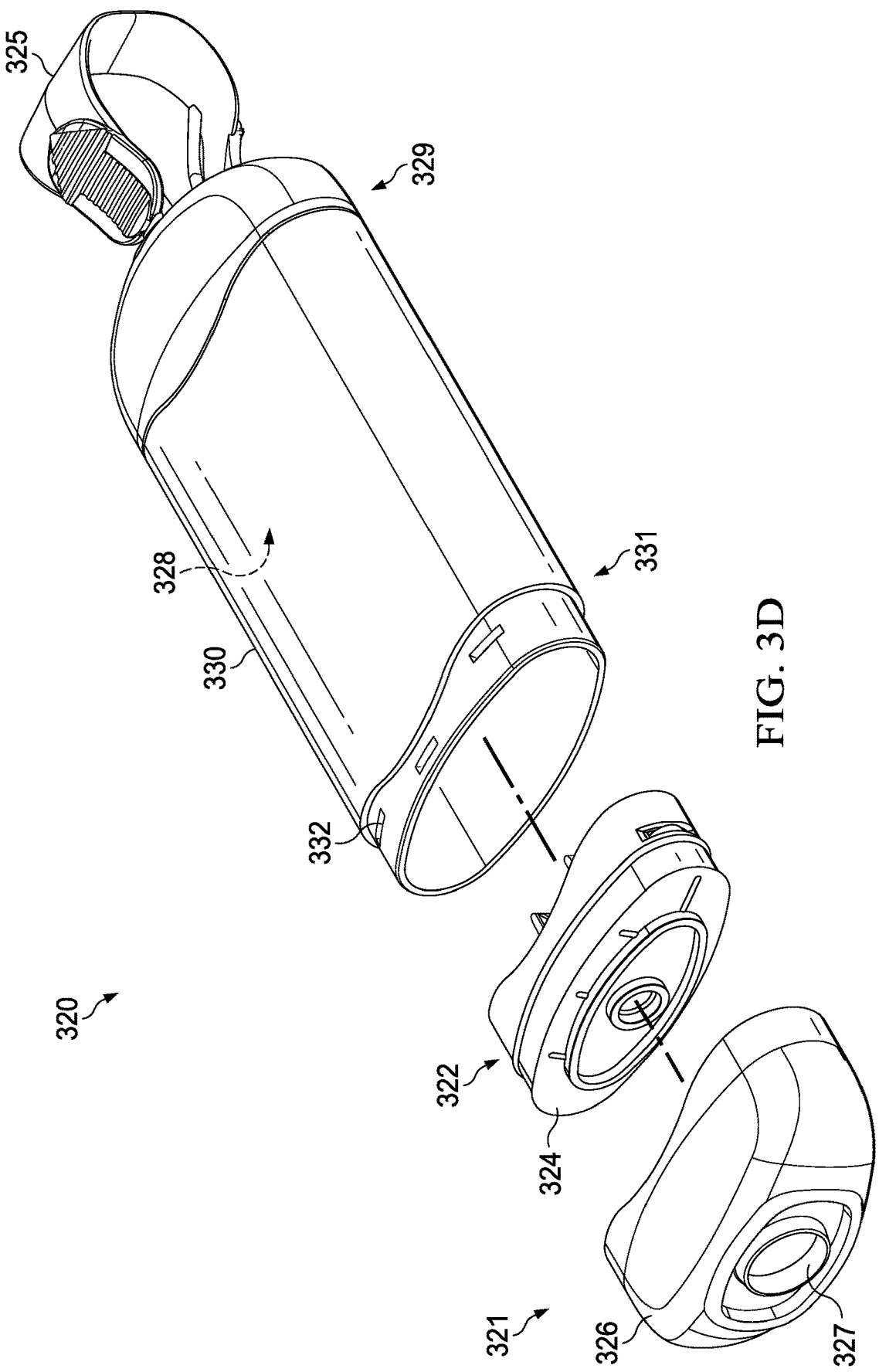
FIG. 3D is a perspective view of another variation of a suction device comprising a storage module comprising a sliding assembly and a sleeve attached to the sliding assembly.

In some variations, a suction device may comprise a housing, a detachable suction force generating mechanism attached to the housing, and a detachable exudates storage module comprising a sleeve (e.g., any of the sleeves described here) and a sliding assembly. The sliding assembly and the suction force generating mechanism may be removed from the suction device along with the sleeve after the ability of the suction device to provide negative pressure is exhausted, and/or after the sleeve is filled with exudates. One example of such a suction device is depicted in FIG. 3D. Suction device 320 may comprise a housing 330, a suction chamber 328 within the housing 330, a detachable suction force generating mechanism (e.g., any of the mechanisms described here, such as constant force springs) releasably attached to the housing 330, and a detachable storage module 321 releasably attached to the housing 330. The suction device 320 may also comprise an activation tool 325 that may be inserted into an aperture located at a proximal portion 329 of the housing 330. The detachable storage module 321 may comprise a distal cap 326 with a distal port 327, a sliding assembly 322, and sleeve 324. The sleeve may or may not have pre-formed creases. The proximal portion of the sleeve 324 may or may not be attached to the sliding assembly 322 and the distal portion of the sleeve 324 may be attached to the distal cap 326 using any of the attachment mechanisms previously described. The storage module 321 may be configured to be inserted into the housing 330 and releasably attached to the housing using any of the attachment mechanisms described above. For example, the housing 330 may have one or more grooves 332 located at a distal portion 331 that may correspond to protrusions (not shown) on the distal cap 326 of the storage module 321. The grooves 332 and protrusions may provide a snap-lock mechanism between the housing 330 and the storage module 321 that releasably attaches the storage module to the housing. Alternatively or additionally, the suction force generating mechanism may be releasably attached to the sliding assembly 322 using any of the previously described attachment mechanisms. Once the storage module 321 is installed in the housing 330, the activation tool 325 may be used to advance the sliding assembly distally to charge the suction device for reduced pressure tissue therapy, thereby charging the suction force generating mechanism. After the ability of the suction device 320 to apply negative pressure has depleted and/or when the sleeve 324 is filled with tissue exudates, the storage module 321, sliding assembly 322 and the suction force generating mechanism may be disengaged from the housing 330. Optionally, the sleeve 324 may be removed. The sleeve 324 may help to sequester the collected exudates so that the other portions of the suction device 320 (e.g., the suction chamber, sliding assembly, and/or distal cap) do not contact the exudates. Once the sleeve has been removed, a new sleeve may be installed for an additional session of reduced pressure tissue therapy. Optionally, the storage module, sliding assembly and suction force generating mechanism may be discarded and a new storage module, sliding assembly and suction force generating mechanism may be installed for an additional session of negative pressure therapy.

Figure 4:
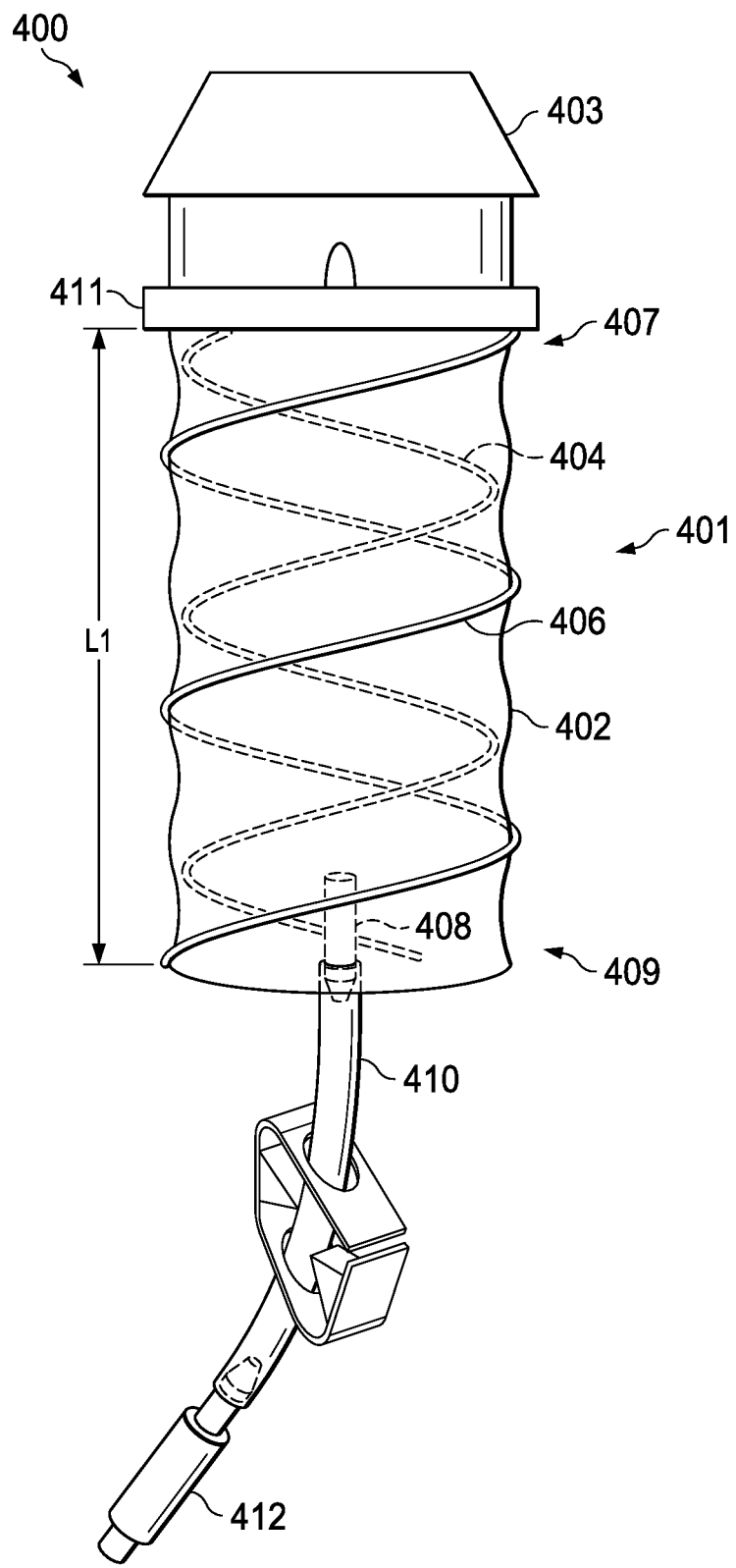
FIG. 4 is another variation of a suction device comprising a storage module comprising a collection pouch with structural support coils.

In some variations, the storage module may comprise a sleeve without a sliding assembly or suction chamber. One example of such a device is depicted in FIG. 4. Suction device 400 may comprise a housing 403 comprising a suction force generating mechanism (not shown) and a storage module 401 comprising a sleeve in the form of a flexible collection pouch 402. The suction force generating mechanism within the housing 403 may comprise, for example, constant force springs that may be attached at their distal ends to a proximal portion 407 of the collection pouch 402. The storage module 401 may be releasably coupled to the constant force springs such that a proximal force applied by the springs may generate negative pressure in the collection pouch. For example, the constant force springs may be fixedly attached to a proximal side of a platform 411 and the collection pouch 402 may be releasably attached to a distal side of the platform 411. The collection pouch 402 may be attached to the platform 411 using any suitable attachment mechanism, for example, using adhesives, clips, screws, hooks and loops, and the like. The platform 411 may be moved distally relative to the housing 403 to extend the constant force springs and charge the suction device 400. In some variations, the collection pouch 402 may comprise an inner coil 404 that spirals along the inner surface of the collection pouch and an outer coil 406 that spirals along the outer surface of the collection pouch. The inner coil 404 and outer coil 406 provide structural support to the collection pouch 402 so that the pouch does not laterally collapse when negative pressure is generated in the collection pouch. For example, the inner coil 404 may provide lateral support by exerting an outward force on the collection pouch. The inner and outer coils may not provide any spring force to the collection pouch that causes or urges the pouch to longitudinally expand from the charged configuration. Other structural components may also be used to help prevent lateral collapse of the collection pouch 402, for example, wire grid scaffolding, meshes, weaves, retention rings, etc. In some variations, the collection pouch 402 may have one or more pre-formed creases, while in other variations, the collection pouch 402 may not have any pre-formed creases.

A distal portion 409 of the collection pouch 402 may comprise a valve 408. The valve 408 may be sized and shaped to interface with any standard tubing or syringe, for example, may be shaped to accommodate a Luer type tubing or syringe fitting. In some variations, the valve 408 may be connected to tubing 410 that may convey negative pressure generated in the collection pouch 402 to a dressing assembly. There may be one or more air flow regulators along the tubing 410, for example, one or more clamps, valves, and/or a syringe 412. The collection pouch 402 may have a length L1 that extends from the proximal portion 407 to the distal portion 409. In a charged configuration, the collection pouch 402 may be longitudinally compressed, and in a depleted configuration, the collection pouch 402 may be longitudinally expanded, where L1 in the charged configuration is less than L1 in the depleted configuration. For example, in the charged configuration, the collection pouch 402 may have a length that is less than the length of the pouch in the depleted configuration. The suction device 400 may be depleted after the collection pouch 402 is no longer able to apply negative pressure to a tissue and/or when the collection pouch 402 is filled with tissue exudates. After the suction device 400 is depleted, the collection pouch 402 may be detached from the constant force springs 403 and disposed. A new collection pouch may be attached to the platform 411 for an additional session of reduced pressure therapy, as may be desirable.

Figure 5A:
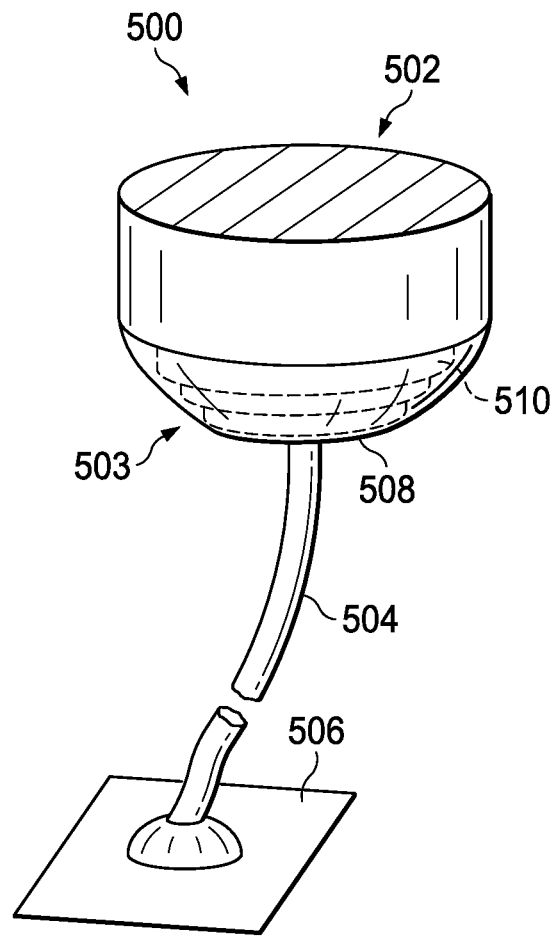
FIGS. 5A and 5B are front perspective views of another variation of a suction device comprising a nested bellows in compressed and expanded configurations, respectively.
Figure 5B:
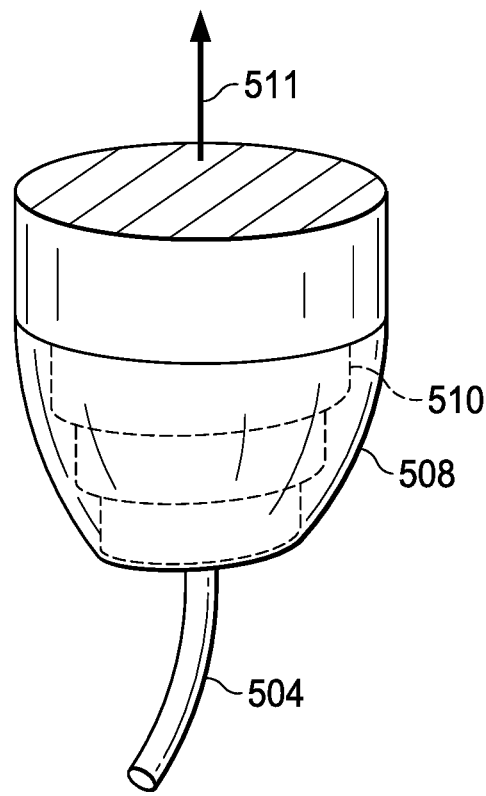

The suction devices described herein may optionally comprise bellows of various geometries. Bellows may have a geometry that approximates the geometry of the suction chamber and/or storage module. For example, a suction device with a suction chamber that is generally cylindrical with an elliptical cross-section may comprise bellows that are similarly cylindrical having an elliptical cross-section. In other variations, bellows that may be included in a storage module of a suction device may have a tapered or conical geometry, such as nested bellows 500 depicted in FIGS. 5A and 5B. Bellows 500 may comprise a helical coil 510 that is encased in a membrane covering 508. The membrane covering 508 may be an elastomeric material that forms a fluid-tight seal around the helical coil 510. The helical coil may provide little to no spring force to the membrane covering to cause or urge the bellows to longitudinally expand. The proximal portion 502 of the bellows 500 may be attached to a suction force generating mechanism (not shown), such as constant force springs, using any attachment mechanism previously described. The distal portion 503 of the bellows 500 may comprise tubing 504 that may provide fluid communication between a dressing assembly 506 at the tissue site and the internal volume of the bellows 500. FIG. 5A depicts the bellows 500 in a compressed, charged configuration, where the bellows are primed to generate negative pressure that may be transmitted to the dressing assembly 506. As the bellows 500 apply negative pressure to the dressing assembly 506, the helical coil 510 may be pulled in a proximal direction 511 and expanded to maintain the application of negative pressure to the dressing assembly. FIG. 5B depicts the bellows 500 in a fully expanded, depleted configuration, where the bellows 500 may no longer be capable of providing negative pressure to the dressing assembly 506. The bellows 500 may also contain tissue exudates that may have been collected during the reduced pressure therapy. In some variations, depending on the quantity of exudates collected in the bellows 500, the ability of the bellows to apply negative pressure to the dressing assembly may be depleted before the helical coil 510 is fully expanded. In some variations, the bellows may comprise support structures of other configurations (e.g., retention rings) to prevent lateral buckling or collapse during negative pressure, wherein the support structures have a shape that corresponds to the cross-sectional geometry of the bellows.

As described above, the storage module of a suction device may be attached to the housing of the suction device using a variety of mechanisms and in a variety of locations. In some variations, the walls of the storage module (e.g., walls of a suction chamber and/or distal cap) may comprise tabs, protrusions, hooks, loops, ridges, recesses, and the like that correspond to structures on the housing that are configured to mechanically engage these features. A storage module may be engaged to the rest of the suction device by attaching the suction force generating mechanism in the housing to a sliding assembly and/or sleeve of the storage module. In some variations, the attachment mechanism between the suction device housing and the storage module may be configured such that the storage module is automatically disengaged when the ability of the suction device to generate negative pressure is depleted. The suction device housing and the storage module may be configured to automatically disengage even before the suction device is completely depleted, as may be desirable.

Figure 6A:
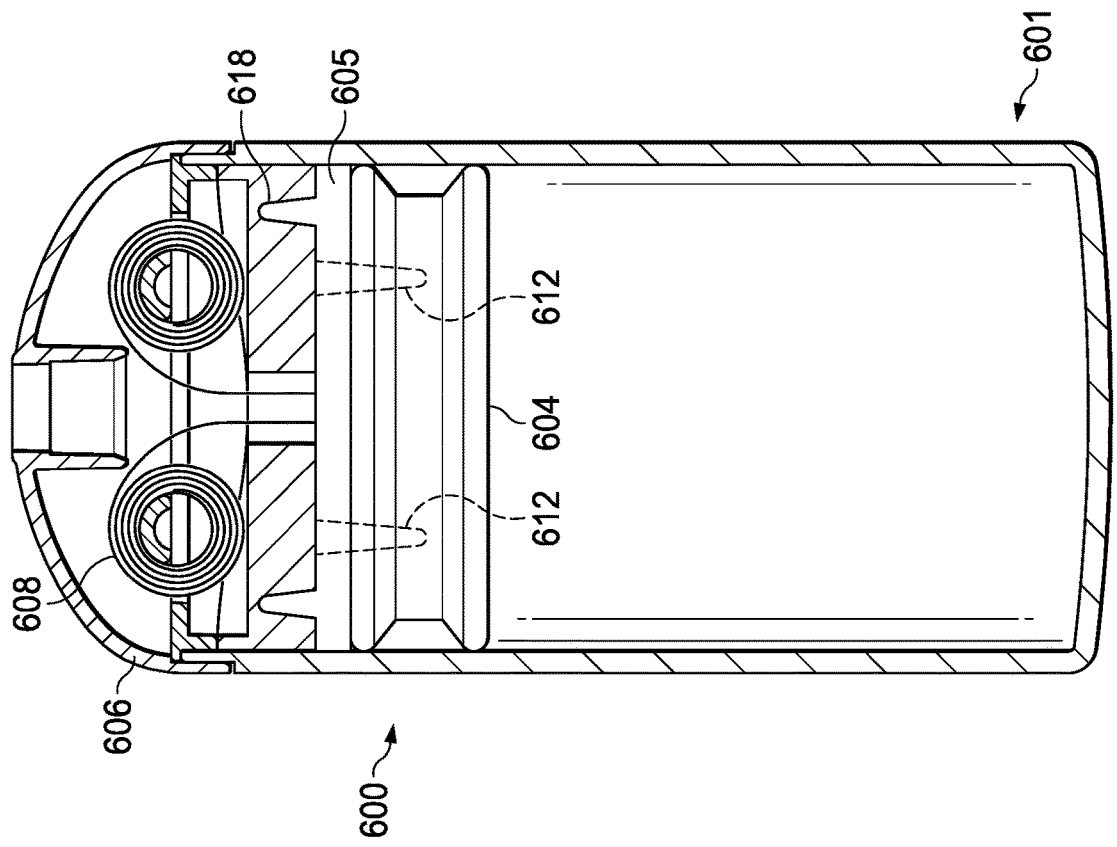
FIGS. 6A and 6B are cross-sectional schematic views of a suction device comprising an attachment mechanism configured to automatically disengage the storage module from the housing when the device is depleted.
Figure 6B:
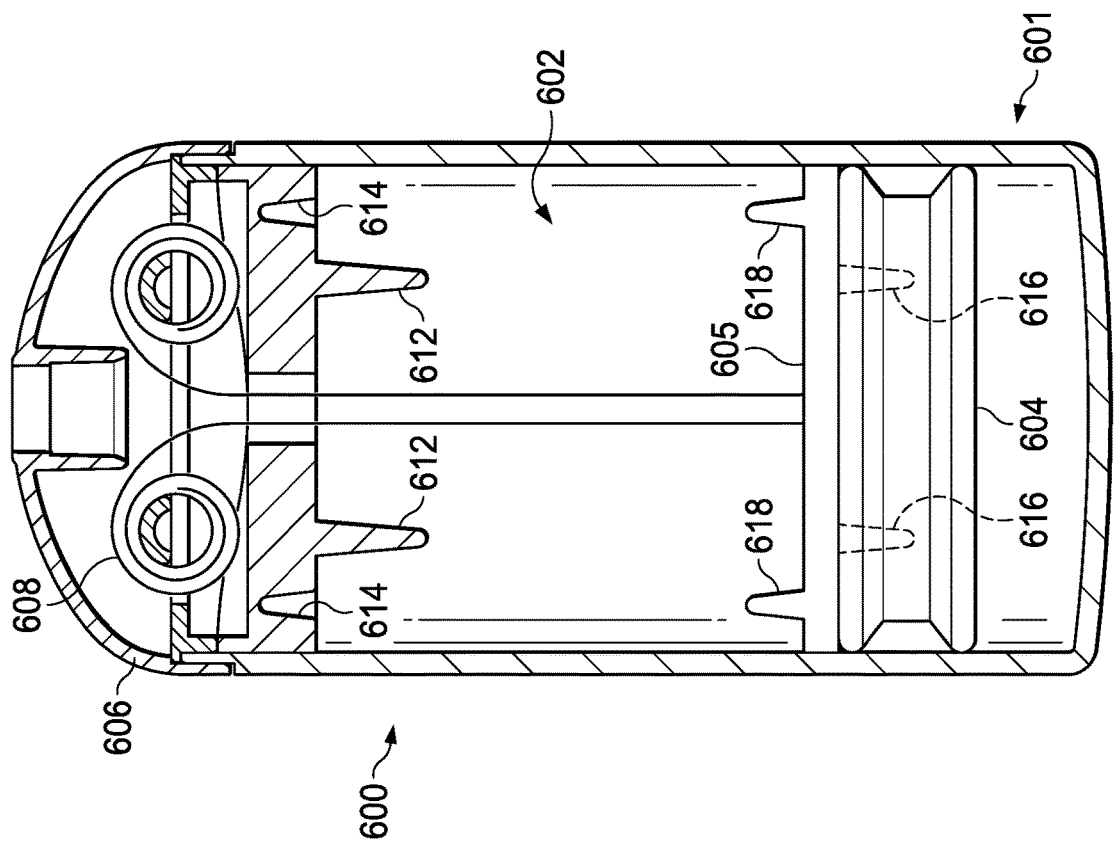

One variation of an attachment mechanism configured to automatically disengage when the suction device is depleted is depicted in FIGS. 6A and 6B. In the variation depicted there, the attachment of internal components (e.g., spring block to the sliding seal assembly) and the attachment of external components (e.g., the suction device housing to the suction chamber of the storage module) may be triggered to automatically disengage. FIG. 6A depicts a partial cutaway view a suction device 600 comprising a housing 606, suction force generating mechanism (e.g., constant force springs 608), and a storage module 601. The constant force springs 608 may be attached to a spring block 605. The suction device housing 606 may comprise one or more protrusions 612 and recesses 614 at a proximal portion of the housing. The housing protrusions 612 may correspond in size and shape with sliding seal assembly recesses 616, and the housing recesses 614 may correspond in size and shape with spring block protrusions 618. The protrusions and recesses on the housing 606 and the spring block 605 may be aligned such that the protrusions may mate with a recess when the spring block 605 is proximally retracted. The storage module 601 may comprise a suction chamber 602 and a sliding seal assembly 604 movable in the suction chamber. The sliding seal assembly 604 may be releasably attached to the spring block 605 by snap-fit, where the engagement of the snap-fit mechanism may be controlled by the presence or absence of the housing protrusions 612 in the sliding seal assembly recesses 616. For example, insertion of the housing protrusion 612 into the sliding seal assembly recess 616 may deflect the snap-fit mechanism such that the spring block 605 may be released from the sliding seal assembly 604. Removal of the housing protrusion 612 may allow the snap-fit mechanism to remain in an engaged configuration so that the spring block and the sliding seal assembly may be attached to each other.

The suction chamber 602 may also be attached to the suction device housing 606 by a snap-fit mechanism. The engagement of the snap-fit mechanism may be controlled by the presence or absence of the spring block protrusions 618 in the housing recesses 614, similar to the mechanism described above for the snap-fit attachment between the spring block 605 and sliding seal assembly 604. The length of the protrusions 612, 618 may be selected such that the disengagement of the storage module 601 from the suction device housing 606 may not occur until the suction device is in a depleted configuration. When the suction device 600 is in a depleted configuration as depicted in FIG. 6B, the spring block protrusions 618 may mate with the housing recesses 614 and disengage the attachment between the housing 606 and suction chamber 602. Additionally, the housing protrusions 612 may mate with the sliding seal assembly recesses 616 and disengage the attachment between the spring block 605 and the sliding seal assembly 604. The length of the protrusions 612, 618 may be the same so that both the attachment mechanisms described here may be disengaged substantially simultaneous. However, the length of the protrusions 612, 618 may be different, if it is desirable for one attachment mechanism to be to be disengaged before the other.

In other variations, the attachment mechanism between the spring block and sliding seal assembly may be configured to be automatically disengaged after the sliding seal assembly has moved across a selected length of the suction chamber. For example, the suction device housing may comprise prongs that extend from the proximal end and the spring block may comprise fingers on a surface facing the proximal end of the housing. The fingers may be located such that they are in alignment with the prongs. The fingers may each be coupled to a spring, such that applying force to the fingers act to compress the spring and release the attachment between the spring block and sliding seal assembly, and releasing the force may allow the fingers to rebound and engage a sliding seal assembly. Initially, the fingers of the spring block may be pressed to attach the sliding seal assembly. As the spring block moves proximally during reduced pressure tissue therapy, the prongs on the suction device housing may contact the fingers on the spring block and compress the springs coupled to the fingers. Compression of the spring may release the attachment between the spring block and sliding seal assembly. The prongs may have any desirable length such that the spring block and the sliding seal assembly may be disengaged after the suction device has been depleted to a certain selected state. An activation tool may be used to engage and disengage the spring block with the sliding seal assembly, as described above. In some embodiments, the distal cap of a storage module and the suction device housing may have any combination of the mechanical features described above to engage the storage module to the suction device housing.

While the suction devices described above generate negative pressure by using one or more constant force springs, it should be understood that any suitable mechanism may be used with a suction device in order to provide negative pressure to a sealed wound enclosure. For example, negative pressure may be generated using a bellows chamber. In the charged configuration, the bellows may be compressed, and as the bellows expands, negative pressure may be transmitted to the tissue. In the depleted configuration, the bellows may be expanded, and may have collected some tissue exudates therein.

Any of the detachable exudate storage modules described above may optionally comprise a fluid retention mechanism to resist or prevent leakage of the exudates that have been collected in the storage module. The fluid retention mechanism may help to reduce the risk of contamination to users or healthcare personnel and their surroundings. The storage module may have a fluid retention assembly comprising an absorbent material so that when the exudates come into contact with the absorbent material, it is absorbed by the material and retained within the storage module. Optionally, the fluid retention assembly may be contained in a mesh and/or screen and/or bag. For example, one variation of a fluid retention assembly may comprise a screen or mesh that may be used to sequester the absorbent material in a certain portion of the storage module and/or suction chamber. The screen or mesh may help to prevent the absorbent material from exiting the storage module and/or suction chamber. Additionally or alternatively, a fluid retention assembly may comprise a pouch that encloses an absorbent material and/or solidifying agent.

Absorbent materials that may be used in a fluid retention assembly may be selected according to the expected viscosity (or other liquid characteristic) and/or quantity of the exudates. Certain absorbent materials may also be selected based on the desired absorption capacity. The absorption capacity of the material may be maintained under negative and/or positive pressure conditions. Some variations of an absorption material may hygroscopic, and may be able to absorb vapor. The fluid absorption material may be permeable to air, such that the negative pressure generated by the suction device may be conveyed to the wound without substantial hindrance. Suitable absorbent materials may be selected from natural, synthetic, and modified natural polymers and materials. Absorbent materials may be inorganic materials, such as silica gels, or organic compounds, such as cross-linked polymers. Other examples of absorbent materials may include gauze, pulp, sponges, dessicated hydrogels, and cross-linked polyprotic resins. Suitable absorbent and/or solidifying materials may be available from various commercial vendors, such as Dow Chemical Company located in Midland, Mich., U.S.A., and Stockhausen GmbH & Co. KG, D-47805 Krefeld, Federal Republic of Germany, and may include sodium polyacrylate with sodium dichloro-S-triazinetrione dihydrate, cellulose based substrates, AQUA KEEP® polymer products, etc. Some variations of a fluid retention assembly may use a superabsorbent material, which may be capable of retaining an amount of water equal to at least 100% of its dry weight (e.g., as measured by the test of Intrinsic Absorbent Capacity). In some of the foregoing embodiments, the superabsorbent material may be Isolyser™ by Microtek Medical. Other examples of fluid retention assemblies are described in U.S. patent application Ser. No. 13/245,744 filed on Sep. 26, 2011, which is hereby incorporated by reference in its entirety and included in the Appendix.

Optionally, some variations of a fluid retention assembly may comprise a disinfectant, which may help to sanitize liquid exudates that enter the storage module and/or suction chamber. For example, the disinfectant may be attached to, embedded in, cross-linked and/or otherwise incorporated with the absorbent material. In other examples, the disinfectant may be freely disposed within the collection chamber, or may be attached to other structures, such as the sliding seal. The disinfectant may be anti-bacterial (e.g. bacteriostatic or bacteriocidal), anti-viral, anti-fungal, and/or anti-parasitic. Some examples of disinfectant compounds that may be used in a fluid retention system may include chlorhexidine, sodium hypochlorite, sodium dichloro-s-triazinetrione dehydrate (or other chlorine-based disinfectant), a sulfonamide, silver sulfadiazine, polyhexanide. In some variations, the absorbent material itself may also act as a disinfectant. For example, a fluid retention assembly may use a liquid medical waste solidifier, such as Isolyser LTS-Plus® Solidifier or Isosorb® Solidifier by Microtek Medical. Optionally, the fluid retention assembly may also comprise a deodorizer, such as zeolite, activated charcoal, silica gel, or hydrogen peroxide. In some variations, the disinfectant may permit disposal of the expended device into regular trash disposal, rather than as biohazardous waste. Other examples and descriptions of fluid retention assemblies (e.g., biohazard containment assemblies) are described in U.S. Pat. Appl. No. 61/372,837, filed on Aug. 11, 2010, which is hereby incorporated by reference in its entirety and included in the Appendix, and U.S. patent application Ser. No. 13/245,744, filed on Sep. 26, 2011, which has been previously incorporated by reference in its entirety.

As noted earlier, examples of prior art systems employing bellows are disclosed in U.S. Pat. Nos. 4,578,060, 4,278,089, 8,641,692, and 8,007,257. Any of the support elements described herein, including structural supports (e.g., retention rings) and/or hinges (e.g., living hinges, mechanical hinges, and hinges with modified geometries, such as increased cross-sectional widths) may be included in the bellows of these prior art designs and other typical wound drainage system designs in order to help to maintain the lateral structural integrity and/or cross-sectional geometry of the bellows under negative pressure.

Although the embodiments herein have been described in relation to certain examples, various additional embodiments and alterations to the described examples are contemplated within the scope of the invention. Thus, no part of the foregoing description should be interpreted to limit the scope of the invention as set forth in the following claims. For all of the embodiments described above, the steps of the methods need not be performed sequentially. Accordingly, it is not intended that the invention be limited, except as by the appended claims.

What is claimed as new and desired to be protected by Letters Patent of the United States is:

1. A reduced pressure therapy device comprising:
   a housing comprising a suction force generating mechanism;
   a distal port;
   a suction chamber;
   a storage module comprising a sleeve including an internal compartment configured to collect exudates through the distal port, wherein the sleeve is configured to provide a barrier between the exudates and the suction chamber, wherein the sleeve has a wall and a support element along the wall configured to resist inward collapse of the wall under negative pressure, and wherein a proximal end wall of the sleeve is attached to the suction force generating mechanism; and
   a fluid retention assembly including a pouch positioned within the internal compartment and configured to retain exudates within the storage module.

2. The device of claim 1, wherein the wall of the sleeve is flexible and the support element comprises a support structure that is more rigid than the flexible wall.

3. The device of claim 2, wherein the support structure comprises a helical coil.

4. The device of claim 2, wherein the support structure comprises one or more rings or loops.

5. The device of claim 2, wherein the support structure comprises wire grid scaffolding.

6. The device of claim 2, wherein the support structure comprises a mesh or weave.

7. The device of claim 1, wherein the support element comprises hinges.

8. The device of claim 7, wherein the hinges comprise living hinges.

9. The device of claim 7, wherein the hinges comprise mechanical hinges comprising discrete components that are pivotally connected by a connecting structure.

10. The device of claim 9, wherein the mechanical hinges include engaging structures that lock the hinge in a desired maximum open angle.

11. The device of claim 9, wherein the mechanical hinges include interfering features that limit the maximum angle to which the hinge can open.

12. The device of claim 1, wherein the wall of the sleeve comprises a plurality of first pleats, wherein each first pleat is perpendicular to a longitudinal axis of the device and defines a first angle.

13. The device of claim 12, wherein the support element is located along at least one first pleat.

14. The device of claim 13, wherein the support element comprises a second material added to the sleeve wall at the first pleat, wherein the second material defines a second pleat having a second angle more acute than the first angle.

15. The device of claim 13, wherein the support element comprises a second material extending from the first pleat and protruding perpendicularly to a longitudinal axis of the sleeve for a distance between about 0.005 inches and about 0.02 inches.

16. The device of claim 15, wherein the distance is between about 0.01 inches and about 0.015 inches.

17. The device of claim 2, wherein the support structure is enclosed within the wall of the sleeve.

18. The device of claim 2, wherein the support structure is located on an inner surface of the wall of the sleeve.

19. The device of claim 2, wherein the support structure is located on an outer surface of the wall of the sleeve.

20. The device of claim 2, wherein the support structure is located on an inner surface and an outer surface of the wall of the sleeve.

21. The device of claim 1, wherein the sleeve further comprises a distal valve.

22. The device of claim 21, wherein the distal valve is a one-way valve.

23. The device of claim 1, wherein the suction force generating mechanism comprises a force member.

24. The device of claim 23, wherein the force member comprises a constant force spring.

25. The device of claim 23, wherein the force member comprises a variable force spring.

26. The device of claim 1, further comprising a sliding assembly translatable along the longitudinal axis of the housing.

27. The device of claim 26, wherein the sliding assembly is a sliding seal assembly.

28. The device of claim 26, wherein the sliding assembly is attached to the suction force generating mechanism.

29. The device of claim 26, wherein the proximal end wall of the sleeve is attached to the sliding assembly by snap-fit, screw-fit, twist-fit, friction-fit, adhesives, hooks and loop engagement, magnetic engagement, clips, and/or clasps.

30. The device of claim 26, further comprising an activation tool configured to urge the sliding assembly distally along a longitudinal axis of the housing.

31. The device of claim 1, wherein the sleeve is detachable from the suction force generating mechanism and the distal port.

32. The device of claim 1, wherein the sleeve wall comprises a film or membrane.

\* \* \* \* \*